(12) United States Patent
Stopek

(10) Patent No.: US 8,453,652 B2
(45) Date of Patent: Jun. 4, 2013

(54) METHODS OF USING SHAPE MEMORY ALLOYS FOR BUTTRESS ATTACHMENT

(75) Inventor: Megan L. Stopek, Yalesville, CT (US)

(73) Assignee: Covidien LP, Mansfieled, MA (US)

( * ) Notice: Subject to any disclaimer, the term of this patent is extended or adjusted under 35 U.S.C. 154(b) by 0 days.

(21) Appl. No.: 13/584,186

(22) Filed: Aug. 13, 2012

(65) Prior Publication Data

US 2012/0305626 A1 Dec. 6, 2012

Related U.S. Application Data

(63) Continuation of application No. 13/228,045, filed on Sep. 8, 2011, now Pat. No. 8,245,901, which is a continuation of application No. 12/442,151, filed as application No. PCT/US2007/022713 on Oct. 25, 2007, now Pat. No. 8,023,883.

(60) Provisional application No. 60/854,821, filed on Oct. 26, 2006.

(51) Int. Cl.
*A61B 17/068* (2006.01)
(52) U.S. Cl.
USPC ............................ 128/898; 227/19; 227/176.1
(58) Field of Classification Search
USPC ....................... 227/176.1, 19, 175.1; 128/898
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |

(Continued)

FOREIGN PATENT DOCUMENTS

| | | |
|---|---|---|
| DE | 199 24 311 | 11/2000 |
| DE | 199 24 311 A1 | 11/2000 |

(Continued)

OTHER PUBLICATIONS

International Search Report corresponding to European Application No. EP 12 15 2229.6, completed on Feb. 23, 2012 and mailed on Mar. 1, 2012; 4 pages.

(Continued)

*Primary Examiner* — Brian D Nash

(57) ABSTRACT

A surgical stapling device includes a tissue contacting surface and a buttress attachment feature. The buttress attachment feature permits selectively securing a surgical buttress to the tissue contacting surface, which may be disposed on a cartridge assembly or an anvil plate of the surgical stapling device. The buttress attachment feature may include a shape memory alloy, such as a nickel titanium alloy, that is responsive to a temperature change to allow the buttress attachment feature to move between a first position where a free end of the buttress attachment feature is substantially spaced from the tissue contacting surface, and second position where the surgical attachment feature is approximated with respect to the tissue contacting surface.

18 Claims, 16 Drawing Sheets

U.S. PATENT DOCUMENTS

| | | |
|---|---|---|
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A * | 4/1996 | Cooper et al. .............. 623/11.11 |
| 5,542,594 A | 8/1996 | McKean et al. |
| 5,549,628 A * | 8/1996 | Cooper et al. ................ 606/220 |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A * | 5/1998 | Francis et al. ................ 606/151 |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A * | 5/1999 | Frater et al. ................... 606/148 |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | Mckean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 * | 12/2001 | Hamilton et al. ............. 606/151 |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,620,166 B1 * | 9/2003 | Wenstrom et al. ............. 606/232 |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 * | 12/2006 | Shelton, IV ................ 227/176.1 |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 7,942,890 B2 | 5/2011 | D'Agostino et al. |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 * | 11/2002 | Grant et al. .................... 606/151 |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0220592 A1 | 11/2004 | Mueller et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2005/0251164 A1 | 11/2005 | Gifford, II et al. |
| 2006/0004407 A1 | 1/2006 | Hiles et al. |
| 2006/0025816 A1 * | 2/2006 | Shelton ........................ 606/215 |
| 2006/0085034 A1 | 4/2006 | Bettuchi |
| 2006/0135992 A1 | 6/2006 | Bettuchi et al. |
| 2006/0173470 A1 * | 8/2006 | Oray et al. .................... 606/151 |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A1 | 3/2007 | Shimoji et al. |

| | | | | | | |
|---|---|---|---|---|---|---|
| 2007/0123839 | A1 | 5/2007 | Rousseau et al. | EP | 1759640 | 3/2007 |
| 2007/0179528 | A1* | 8/2007 | Soltz et al. ............... 606/219 | EP | 1621141 | 7/2007 |
| 2007/0203509 | A1 | 8/2007 | Bettuchi | EP | 1 815 804 A2 | 8/2007 |
| 2007/0203510 | A1 | 8/2007 | Bettuchi | EP | 1994890 | 11/2008 |
| 2007/0246505 | A1 | 10/2007 | Pace-Floridia et al. | EP | 2 008 595 A2 | 12/2008 |
| 2008/0029570 | A1 | 2/2008 | Shelton et al. | EP | 2005894 | 12/2008 |
| 2008/0082126 | A1 | 4/2008 | Murray et al. | EP | 2005895 | 12/2008 |
| 2008/0110959 | A1 | 5/2008 | Orban et al. | EP | 2 198 787 A1 | 6/2010 |
| 2008/0125812 | A1 | 5/2008 | Zubik et al. | EP | 2 236 098 A2 | 10/2010 |
| 2008/0140115 | A1 | 6/2008 | Stopek | JP | 2000-166933 | 6/2000 |
| 2008/0161831 | A1 | 7/2008 | Bauman et al. | JP | 07-124166 | 5/2007 |
| 2008/0161832 | A1 | 7/2008 | Bauman et al. | WO | WO 90/05489 | 5/1990 |
| 2008/0169327 | A1 | 7/2008 | Shelton et al. | WO | WO 96/22055 A1 | 7/1996 |
| 2008/0169328 | A1 | 7/2008 | Shelton | WO | WO97/01989 | 1/1997 |
| 2008/0169329 | A1 | 7/2008 | Shelton et al. | WO | WO 97/13463 | 4/1997 |
| 2008/0169330 | A1 | 7/2008 | Shelton et al. | WO | WO 98/17180 | 4/1998 |
| 2008/0169331 | A1 | 7/2008 | Shelton et al. | WO | WO 99/45849 | 9/1999 |
| 2008/0169332 | A1 | 7/2008 | Shelton et al. | WO | WO 03/082126 A1 | 10/2003 |
| 2008/0169333 | A1 | 7/2008 | Shelton et al. | WO | WO 03/105698 A2 | 12/2003 |
| 2008/0290134 | A1 | 11/2008 | Bettuchi et al. | WO | WO 03/206698 A2 | 12/2003 |
| 2008/0308608 | A1 | 12/2008 | Prommersberger | WO | WO 2006/023578 | 3/2006 |
| 2008/0314960 | A1 | 12/2008 | Marczyk et al. | WO | WO 2006/044490 | 4/2006 |
| 2009/0001121 | A1 | 1/2009 | Hess et al. | WO | WO 2006/083748 A1 | 8/2006 |
| 2009/0001122 | A1* | 1/2009 | Prommersberger | WO | WO 2007/121579 A1 | 11/2007 |
| | | | et al. ............... 227/176.1 | WO | WO2008/057281 | 5/2008 |
| 2009/0001123 | A1 | 1/2009 | Morgan et al. | WO | WO 2008/109125 | 9/2008 |
| 2009/0001124 | A1 | 1/2009 | Hess et al. | WO | WO 2010/075298 A2 | 7/2010 |
| 2009/0001125 | A1 | 1/2009 | Hess et al. | WO | WO 2011/143183 A2 | 11/2011 |
| 2009/0001126 | A1 | 1/2009 | Hess et al. | WO | WO 2012/044848 A1 | 4/2012 |
| 2009/0001128 | A1 | 1/2009 | Weisenburgh, II et al. | | | |
| 2009/0001130 | A1 | 1/2009 | Hess et al. | | | |
| 2009/0005808 | A1 | 1/2009 | Hess et al. | | | |
| 2009/0030452 | A1 | 1/2009 | Bauman et al. | | | |
| 2009/0043334 | A1 | 2/2009 | Bauman et al. | | | |
| 2009/0076510 | A1 | 3/2009 | Bell et al. | | | |
| 2009/0076528 | A1 | 3/2009 | Sgro | | | |
| 2009/0078739 | A1 | 3/2009 | Viola | | | |
| 2009/0095791 | A1 | 4/2009 | Eskaros et al. | | | |
| 2009/0095792 | A1 | 4/2009 | Bettuchi | | | |
| 2009/0120994 | A1 | 5/2009 | Murray et al. | | | |
| 2009/0134200 | A1 | 5/2009 | Tarinelli et al. | | | |
| 2009/0206125 | A1 | 8/2009 | Huitema et al. | | | |
| 2009/0206126 | A1 | 8/2009 | Huitema et al. | | | |
| 2009/0206139 | A1 | 8/2009 | Hall et al. | | | |
| 2009/0206141 | A1 | 8/2009 | Huitema et al. | | | |
| 2009/0206142 | A1 | 8/2009 | Huitema et al. | | | |
| 2009/0206143 | A1 | 8/2009 | Huitema et al. | | | |
| 2009/0218384 | A1 | 9/2009 | Aranyi | | | |
| 2009/0277947 | A1 | 11/2009 | Viola | | | |
| 2009/0287230 | A1 | 11/2009 | D'Agostino et al. | | | |
| 2010/0012704 | A1 | 1/2010 | Tarinelli Racenet et al. | | | |
| 2010/0065606 | A1 | 3/2010 | Stopek | | | |
| 2010/0065607 | A1 | 3/2010 | Orban, III et al. | | | |
| 2010/0072254 | A1 | 3/2010 | Aranyi et al. | | | |
| 2010/0147921 | A1 | 6/2010 | Olson | | | |
| 2010/0147922 | A1 | 6/2010 | Olson | | | |
| 2010/0147923 | A1 | 6/2010 | D'Agostino et al. | | | |
| 2010/0243707 | A1 | 9/2010 | Olson et al. | | | |
| 2010/0243708 | A1 | 9/2010 | Aranyi et al. | | | |
| 2010/0243711 | A1 | 9/2010 | Olson et al. | | | |
| 2010/0249805 | A1 | 9/2010 | Olson et al. | | | |
| 2010/0264195 | A1 | 10/2010 | Bettuchi | | | |
| 2010/0282815 | A1 | 11/2010 | Bettuchi et al. | | | |
| 2011/0024476 | A1 | 2/2011 | Bettuchi et al. | | | |
| 2011/0024481 | A1 | 2/2011 | Bettuchi et al. | | | |
| 2011/0036894 | A1 | 2/2011 | Bettuchi | | | |
| 2011/0042442 | A1 | 2/2011 | Viola et al. | | | |
| 2011/0046650 | A1 | 2/2011 | Bettuchi | | | |
| 2011/0057016 | A1 | 3/2011 | Bettuchi | | | |
| 2011/0087279 | A1 | 4/2011 | Shah et al. | | | |

FOREIGN PATENT DOCUMENTS

| | | |
|---|---|---|
| EP | 0594148 | 4/1994 |
| EP | 0327022 | 4/1995 |
| EP | 0667119 | 8/1995 |
| EP | 1 520 525 | 4/2005 |
| EP | 1064883 | 8/2005 |
| EP | 1 702 570 A1 | 9/2006 |
| EP | 1256317 | 12/2006 |

OTHER PUBLICATIONS

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

International Search Report from application EP 06016962.0 dated Jan. 3, 2007.

International Search Report from application PCT/US05/36740 mailed Mar. 23, 2007.

International Search Report from Application No. PCT/US2008/002981 dated Jun. 26, 2008.

International Search Report from Application No. EP 08 25 1779 dated Jul. 23, 2008.

European Search Report for application EP 05022585 dated Feb. 3, 2006.

International Search Report EP 10 25 0639 dated Jun. 28, 2010.

International Search Report corresponding to European Application No. EP 06 00 4598, completed on Jun. 22, 2006; 3 pages.

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010; and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report for PCT/US2007/022713 date of completion is Apr. 21, 2008 (2 pages).
International Search Report corresponding to European Application No. EP 11 18 8309.6 completed on Dec. 15, 2011 and mailed on Jan. 12, 2012; 3 pages.

International Search Report No. EP 10250715 dated Jun. 30, 2010.
International Search Report No. EP 10250642 dated Mar. 25, 2011.

* cited by examiner

METHODS OF USING SHAPE MEMORY ALLOYS FOR BUTTRESS ATTACHMENT

CROSS REFERENCE TO RELATED APPLICATIONS

This application is a Continuation Application claiming the benefit of and priority to U.S. patent application Ser. No. 13/228,045, filed on Sep. 8, 2011 (now U.S. Pat. No. 8,245, 901), which is a Continuation Application claiming the benefit of and priority to U.S. patent application Ser. No. 12/442, 151, filed on Mar. 20, 2009 (now U.S. Pat. No. 8,028,883), which is a U.S. National Stage Application filed under 35 U.S.C. §371(a) of International Application No. PCT/US2007/22713, filed on Oct. 25, 2007, which claims the benefit of and priority to U.S. Provisional Patent Application No. 60/854,821 filed on Oct. 26, 2006, the entire content of each application being incorporated by reference herein.

BACKGROUND

1. Technical Field

The present disclosure relates to surgical instruments, devices and methods of using the same and, more particularly, surgical instruments including surgical stapling devices for applying buttress attachments, buttress attachments and methods of using and applying the same.

2. Discussion of Related Art

In some surgical operations, surgical supports or buttresses, e.g., meshes, are employed by surgeons to bridge, repair and/or reinforce tissue defects within a patient, especially those occurring in the abdominal wall, chest wall, diaphragm and other musculo-aponeurotic areas of the body. Surgical supports are disclosed in, e.g., U.S. Pat. Nos. 3,054, 406, 3,124,136, 4,347,847, 4,655,221, 4,838,884 and 5,002, 551. During such operations, surgeons employ conventional or known suturing or anchoring techniques to apply such supports to body tissue. For example, U.S. Pat. Nos. 4,452, 245 and 5,203,864 describe methods for suturing or anchoring mesh supports to body tissue, especially during hernia repair operations.

Surgical instruments including surgical stapling devices are employed by surgeons to sequentially or simultaneously apply one or more rows of surgical fasteners, e.g., staples or two-part fasteners, to body tissue for the purpose of joining segments of body tissue together. Such devices generally consist of a pair of jaws or finger-like structures between which body tissue to be joined is placed. When the instrument is actuated, or "fired," longitudinally moving firing bars contact staple drive members in one of the jaws, thereby pushing surgical staples through the body tissue and into an anvil in the opposite jaw which crimps the staples closed. If tissue is to be removed, a knife blade can be provided to cut between lines of staples. Examples of such instruments are described in U.S. Pat. Nos. 4,354,628, 5,014,899 and 5,040,715, each of which are incorporated herein by reference.

Surgical stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post operative recovery time. Thus, it is advantageous to provide surgical buttresses for use with surgical stapling devices which enhance sealing at the surgical site.

Placement of the surgical buttress in position on the surgical stapling device, prior to insertion of the surgical stapling device into the target surgical site (i.e., through a trocar, cannula, body opening or the like), is desirable in order to best ensure that the surgical buttress is properly positioned on the surgical stapling device.

Accordingly, a need exists for a surgical buttress which is operatively associatable with the surgical stapling device, prior to positioning of the surgical stapling device at the target surgical site, and which surgical buttress is maintained or remains in position relative to the surgical stapling device during positioning of the surgical stapling device, to the target surgical site, through a trocar, cannula, body orifice or the like.

SUMMARY

The present disclosure relates to surgical stapling devices for applying buttress attachments, buttress attachments and methods of using and applying the same.

According to an aspect of the present disclosure, a surgical stapling device is provided and includes a cartridge assembly; an anvil assembly operatively associated with the cartridge assembly and in juxtaposed relation thereto; a first tissue contacting surface defined by at least one of the cartridge assembly and the anvil plate; and a buttress attachment feature for selectively securing a surgical buttress adjacent the first tissue contacting surface. The buttress attachment feature is responsive to a temperature change such that the buttress attachment feature is movable between a first position in which, at a first temperature, a free end of the buttress attachment feature is substantially spaced from the first tissue contacting surface, and a second position in which, at a second temperature, the free end is relatively approximated to the first tissue contacting surface to secure the surgical buttress to the first tissue contacting surface.

The buttress attachment feature may include a plurality of fingers disposed along the first tissue contacting surface. The plurality of fingers may extend along an outer edge of the first tissue contacting surface. The plurality of fingers may extend along at least one of a knife channel formed in the first tissue contacting surface and an outer edge of the first tissue contacting surface.

The plurality of fingers may be oriented to extend substantially orthogonal to the first tissue contacting surface when the buttress attachment feature is in the first position, and substantially parallel to the first tissue contacting surface when the buttress attachment feature is in the second position.

The plurality of fingers may include a shape memory alloy. The shape memory alloy may be a nickel titanium alloy.

The plurality of fingers may be configured to penetrate the surgical buttress when the buttress attachment feature is in the first position, and to overlie the first tissue contacting surface when the buttress attachment feature is in the second position.

The first tissue contacting surface may be defined by the cartridge assembly. The surgical stapling device may further include a second buttress attachment feature for selectively securing a second surgical buttress to a second tissue contacting surface defined by the anvil assembly.

According to another aspect of the present disclosure, a surgical stapling device is provided including a cartridge assembly; an anvil assembly operatively associated with the cartridge assembly and in juxtaposed relation thereto; and a buttress attachment feature. The buttress attachment feature includes a plurality of ribs operatively connected to at least one of the cartridge assembly and the anvil assembly; and a panel supported by the plurality of ribs. The plurality of ribs is moveable between a first position in which the panel is spaced from a tissue contacting surface defined by at least one of the cartridge assembly and the anvil assembly, and a second position in which the panel overlies the tissue contacting surface.

The panel may include a surgical buttress. The plurality of ribs may move between the first position and the second position in response to a temperature change.

The plurality of ribs may include a shape memory alloy that is responsive to temperature changes. The plurality of ribs may each have a first end positioned proximate a midpoint of the tissue contacting surface, and a second end extending away from the first end such that the plurality of ribs define a fan-like configuration.

The buttress attachment feature may include a frame supported on the plurality of ribs and extending around a perimeter of the surgical buttress.

According to yet another aspect of the present disclosure, a method of performing a surgical procedure is provided including the steps of providing a surgical stapling device including a cartridge assembly, an anvil assembly, wherein a tissue contacting surface is defined by at least one of the cartridge assembly and the anvil assembly, and a buttress attachment feature responsive to a change in temperature; exposing the buttress attachment feature to a change in temperature to move the buttress attachment feature from a first position where a free end of the buttress attachment feature is spaced from the tissue contacting surface to a second position where the free end of the buttress attachment feature is relatively proximate to the tissue contacting surface; and introducing the cartridge assembly and the anvil assembly into a target surgical site.

The method may further include the step of introducing a surgical buttress to the tissue contacting surface prior to the step of exposing the buttress attachment feature to a change in temperature.

BRIEF DESCRIPTION OF THE DRAWINGS

Preferred embodiments of the invention are described hereinbelow, wherein.

DETAILED DESCRIPTION OF EMBODIMENTS

Figure 1:
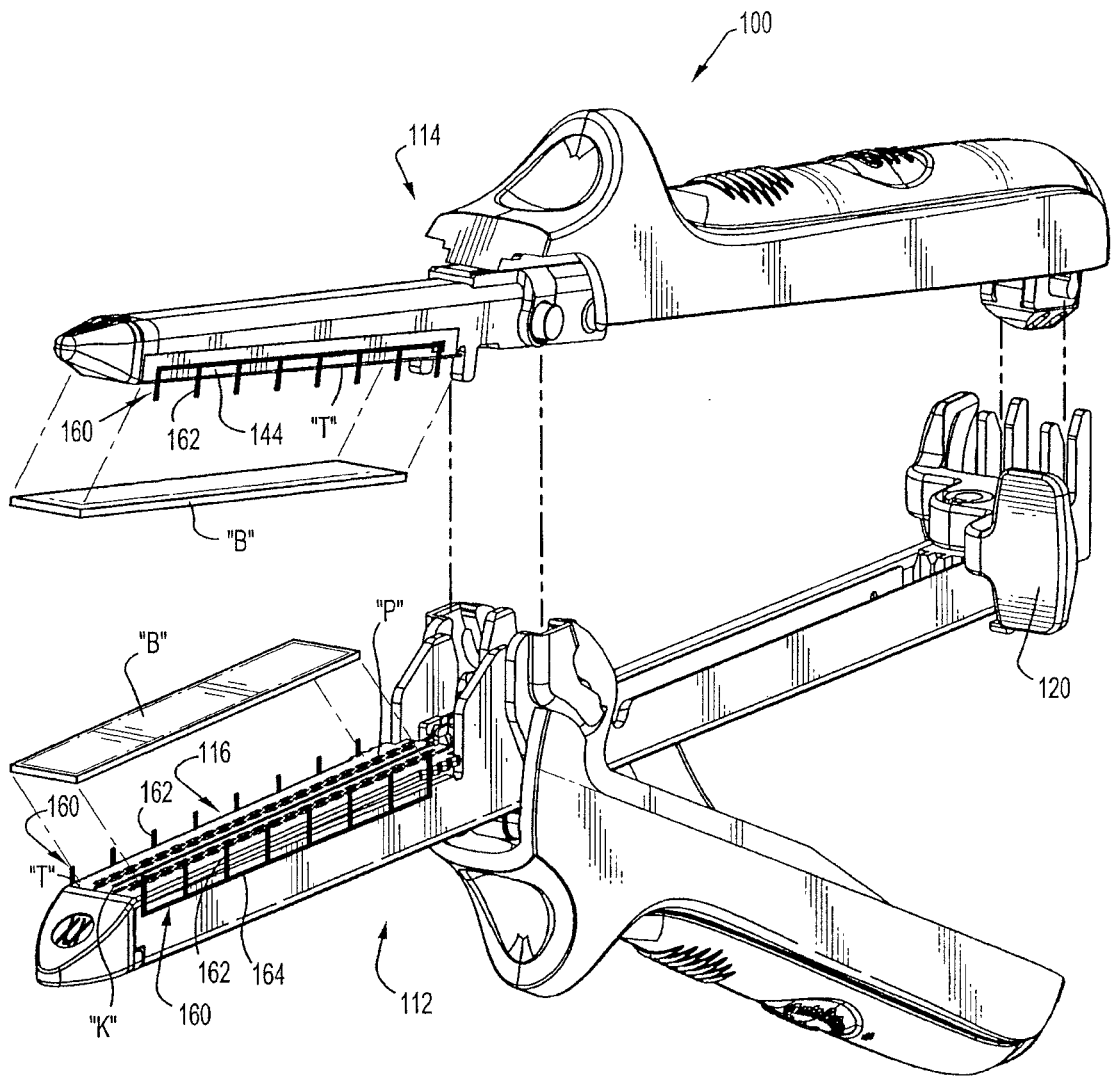
FIG. 1 is a perspective view of a surgical stapling device including a buttress attachment feature, according to an embodiment of the present disclosure, wherein the buttress attachment feature is illustrating in a first condition securing a surgical buttress to a tissue contacting surface of the surgical stapling device.

Preferred embodiments of the presently disclosed surgical stapling devices will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

A surgical stapling device, in accordance with an embodiment of the present disclosure, is shown generally as 100 in FIGS. 1-7. Surgical stapling device 100 includes a cartridge receiving half-section 112, an anvil half-section 114 operatively couplable or connectable to cartridge receiving half-section 112, a cartridge assembly 116 configured and adapted to be removably mounted within a distal end of cartridge receiving half-section 112 and a firing slide 120 configured and adapted to be slidably received within cartridge receiving half-section 112.

As seen in FIG. 1, anvil half-section 114 is provided with an anvil plate 144 configured and dimensioned to be fit over a distal end of anvil half-section 114. Anvil plate 144 includes a plurality of anvil pockets formed therein (not shown), arranged in two pairs of longitudinal rows, and an anvil knife track (not shown) formed longitudinally therealong.

Reference may be made to U.S. patent application Ser. No. 10/508,191, filed Sep. 17, 2004, the entire content of which is incorporated herein by reference, for a more detailed discussion of the structure and operation of surgical stapling device 100.

Figure 2:
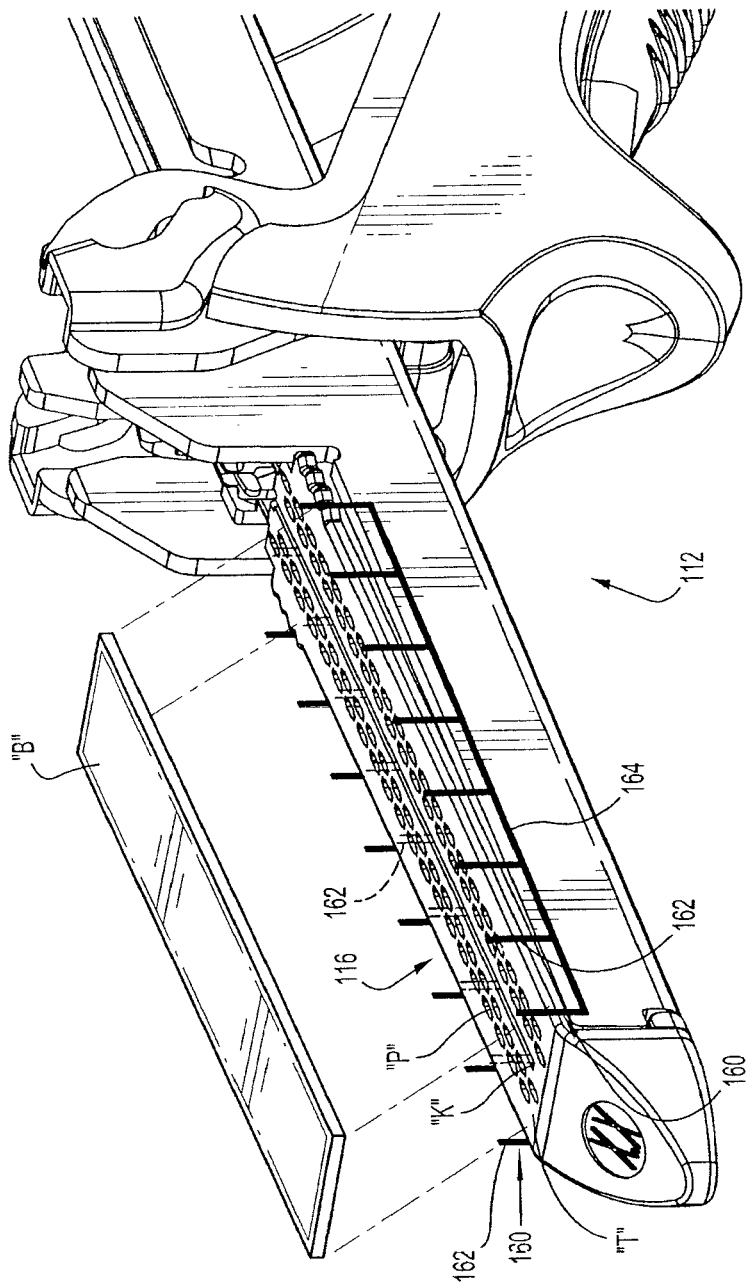
FIG. 2 is an enlarged perspective view of a distal end of the surgical stapling device of FIG. 1, illustrating the buttress attachment feature in a first condition.
Figure 3:
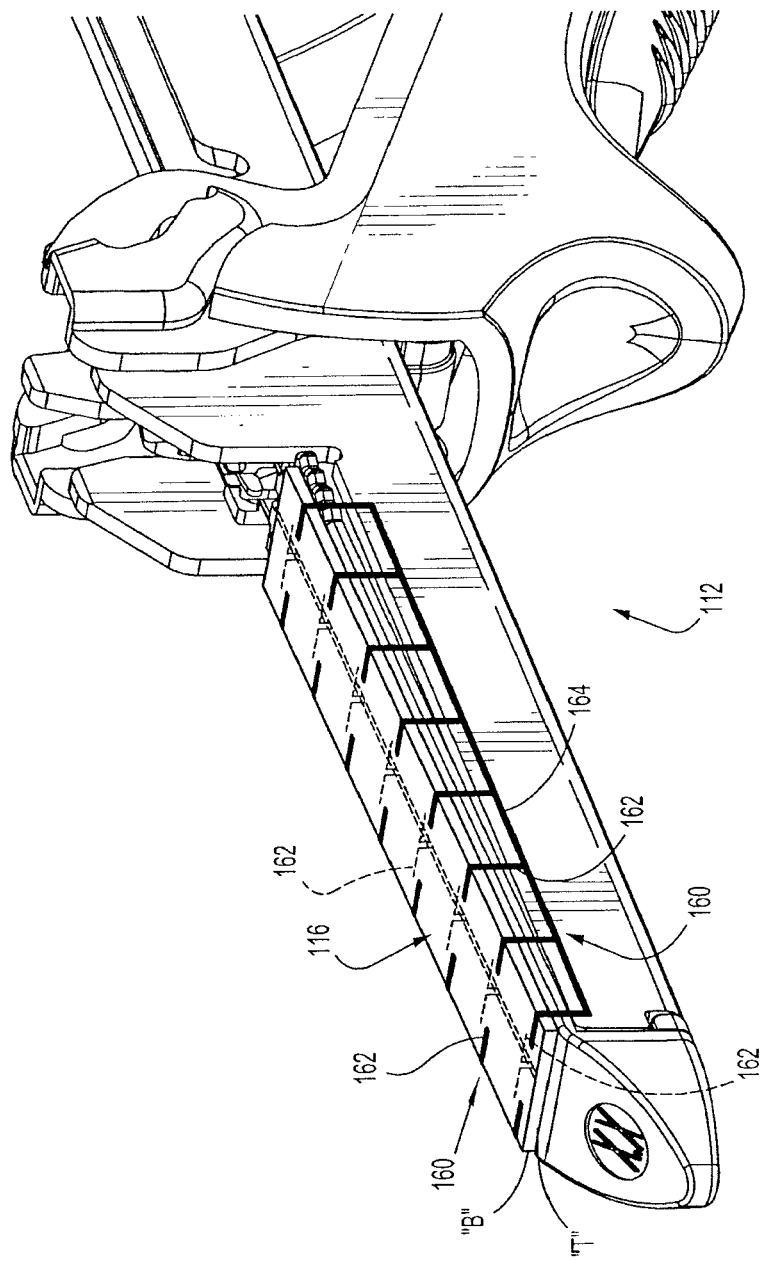
FIG. 3 is an enlarged perspective view of the distal end of the surgical stapling device of FIG. 1, illustrating the buttress attachment feature in a second condition for placement of the surgical buttress into position against the tissue contacting surface of the surgical stapling device.

As seen in FIGS. 1-3, surgical stapling device 100 includes a buttress attachment feature 160 operatively associated with at least one of the distal end of cartridge receiving half-section 112, distal end of anvil half-section 114, cartridge assembly 116 and anvil plate 144. Each buttress attachment feature 160 includes a plurality of fingers 162 positioned along a length of at least one of the distal end of cartridge receiving half-section 112, distal end of anvil half-section 114, cartridge assembly 116 and anvil plate 144. In an embodiment, fingers 162 may be placed along a length of a knife channel "K" formed in cartridge assembly 116 and/or anvil plate 144 (not shown).

In one embodiment, fingers 162 are spaced apart from one another. Fingers 162 function to releasably and/or selectively secure a surgical buttress "B" to a tissue contacting surface "T" of any of the distal end of cartridge receiving half-section 112, distal end of anvil half-section 114, cartridge assembly 116 and anvil plate 144. In one embodiment, as seen in FIGS. 1-3, fingers 162 may be supported on and/or extend from a backspan or crown 164. Backspan 164 may be secured to both side surfaces of distal end of cartridge receiving half-section 112 and/or both side surfaces of distal end of anvil half-section 114.

Fingers 162 have a first position in which fingers 162 extend substantially orthogonally from a tissue contacting surface "T" of any of the distal end of cartridge receiving half-section 112, distal end of anvil half-section 114, cartridge assembly 116 and anvil plate 144. In the first position, fingers 162 are oriented so as to enable and/or allow placement and/or removal of surgical buttress "B" into or out of contact with tissue contacting surfaces "T".

Fingers 162 have a second position in which at least a distal or free end of fingers 162 extend substantially parallel to tissue contacting surface "T" of any of the distal end of cartridge receiving half-section 112, distal end of anvil half-section 114, cartridge assembly 116 and anvil plate 144, in a direction towards staple pockets "P" or anvil pockets (not shown). The anvil pockets are formed in the surface of anvil plate 144 and are in juxtaposed relation to staple pockets "P". In the second position and with a surgical buttress "B" in position against tissue contacting surface "T" of any of the distal end of cartridge receiving half-section 112, distal end of anvil half-section 114, cartridge assembly 116 and anvil plate 144, fingers 162 are oriented so as to prevent movement and/or removal of surgical buttress "B" relative to and/or from tissue contacting surfaces "T" of any of the distal end of cartridge receiving half-section 112, distal end of anvil half-section 114, cartridge assembly 116 and anvil plate 144.

At least fingers 162 of buttress attachment feature 160 is fabricated from a shape memory alloy (i.e., Nickel Titanium, NiTi, Nitinol, etc.), a shape memory polymer, or any other suitable material exhibiting shape memory properties during elevated temperatures. Shape memory alloys, such as NiTi, undergo a phase transformation (i.e., austenite to martensite and vise versa) during temperature fluctuations (i.e., increases and decreases).

In use, as seen in FIGS. 1 and 2, with buttress attachment features 160 at a first temperature, fingers 162 are oriented in the first position, as described above. With fingers 162 in the first position, a surgical buttress "B" may be placed in position against tissue contacting surfaces "T" of anvil plate 144 and/or cartridge assembly 116. With surgical buttress "B" so positioned, the temperature in the proximity of the distal ends of cartridge receiving half-section 112 and/or anvil half-section 114 is varied from the first temperature to a second temperature, i.e., either elevated or reduced relative to the first temperature. At the second temperature, buttress attachment features 160 undergo a phase transformation, as described above, wherein free ends of fingers 162 move to the second position, as described above, to secure, maintain, retain or otherwise hold surgical buttress "B" in contact and in position on tissue contacting surface "T" of cartridge half-section 112 and/or anvil half-section 114.

In one embodiment, surgical buttress "B" is configured and sized such that fingers 162 of buttress attachment features 160 are disposed along outer edges thereof, when in the first position, and the distal ends of fingers 162 deflect down atop a tissue contact surface of surgical buttress "B" when in the second position. In another embodiment, fingers 162 of buttress attachment features 160, when in the first position, may extend substantially orthogonally from tissue contacting surfaces "T" of cartridge assembly 116 and/or anvil plate 144 at a location disposed between a side edge thereof and knife channel "K". In this embodiment, surgical buttress "B" is positioned against tissue contacting surfaces "T" of cartridge assembly 116 and/or anvil plate 144 such that fingers 162 penetrate therethrough (not shown). Moreover, in this embodiment, when the distal ends of fingers 162 are in the second position, the distal ends of fingers 162 may extend toward and/or away from knife channel "K".

In another embodiment, fingers 162 of buttress attachment features 160, as described above, may be positioned along a length of knife channel "K". In this embodiment, surgical buttress "B" is positioned against tissue contacting surfaces "T" of cartridge assembly 116 and/or anvil plate 144 such that fingers 162 penetrate therethrough (not shown). Moreover, in this embodiment, when the distal ends of fingers 162 are in the second position, the distal ends of fingers 162 may extend away from knife channel "K".

With surgical buttress "B" so positioned, the distal end of surgical stapling device 100 may be positioned at the target surgical site with surgical buttress "B" securely held in position against tissue contacting surfaces "T" of cartridge assembly 116 and/or anvil plate 144. Surgical buttress "B" is properly positioned when at least a substantial portion of staple pockets "P" is covered thereby.

Buttress attachment features 160 may be positioned on cartridge receiving half-section 112 and/or anvil half-section 114 in such a manner so as to not increase an outer circumferential profile of the distal ends thereof. In this manner, buttress attachment features 160 do not interfere with the placement of the distal end of surgical stapling device 100 at the target surgical site. For example, with buttress attachment features 160 positioned along knife channel "K" (as shown in phantom in FIGS. 2 and 3), buttress attachment features 160 do not, at any time, extend beyond an outer profile of distal ends of cartridge receiving half-section 112 and/or anvil half-section 114.

Figure 4:
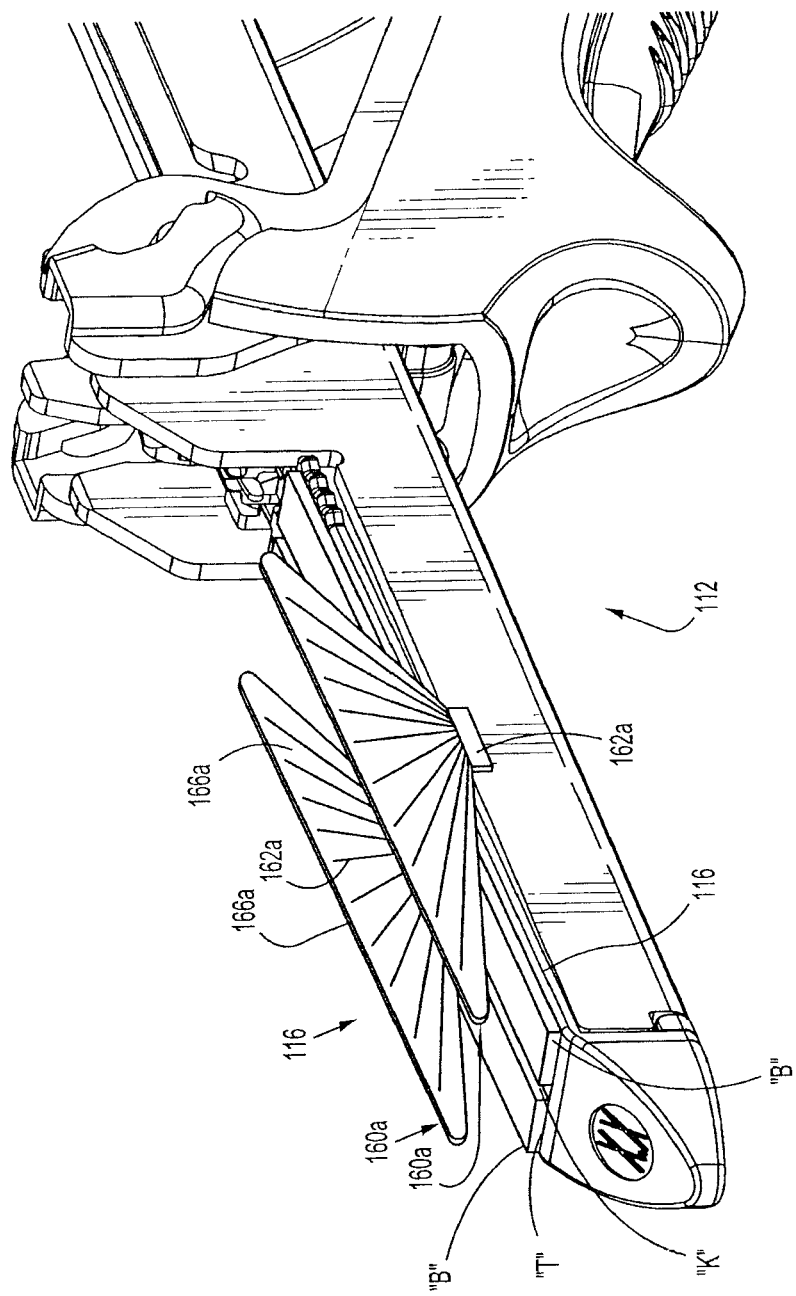
FIG. 4 is an enlarged perspective view of a distal end of the surgical stapling device of FIG. 1, illustrating a buttress attachment feature according to another embodiment of the present disclosure, shown in a first condition.
Figure 4A:
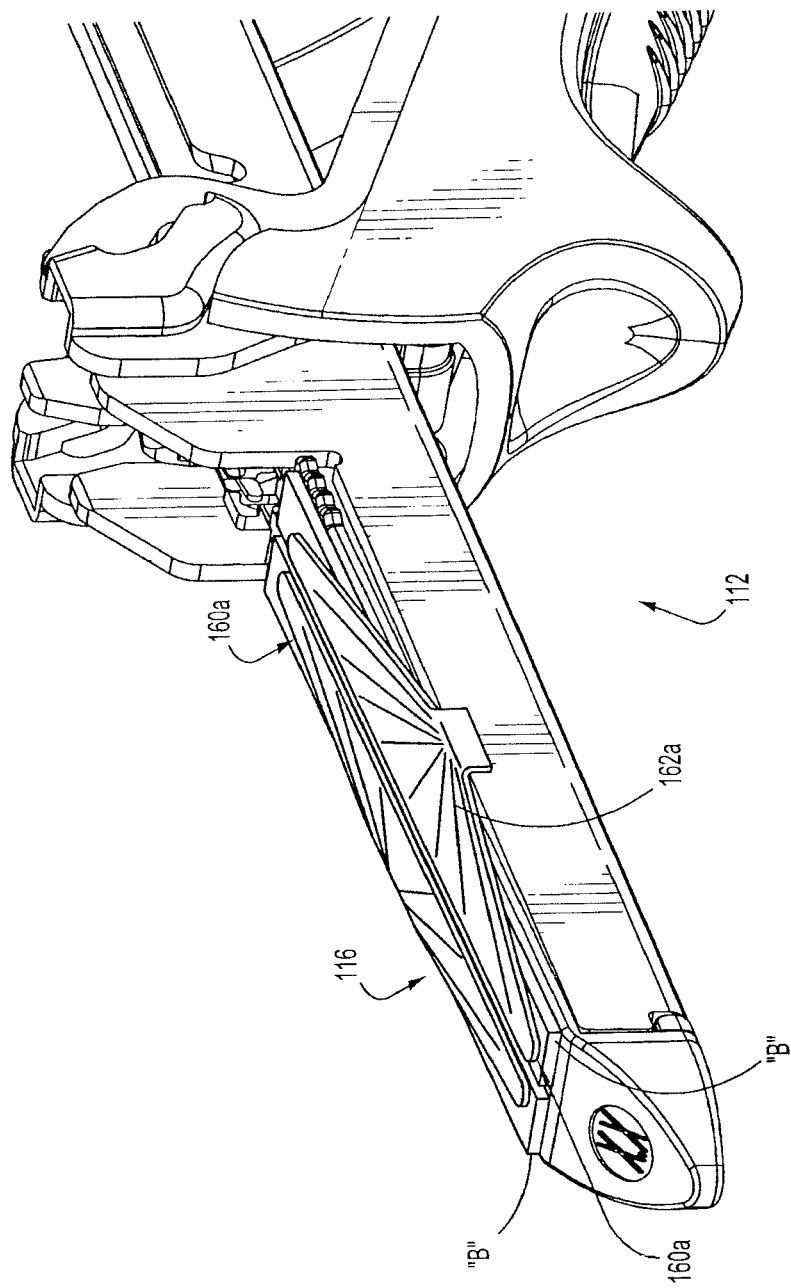
FIG. 4A is an enlarged perspective view of the distal end of the surgical stapling device of FIG. 4, illustrating the buttress attachment feature thereof in a second condition.
Figure 5:
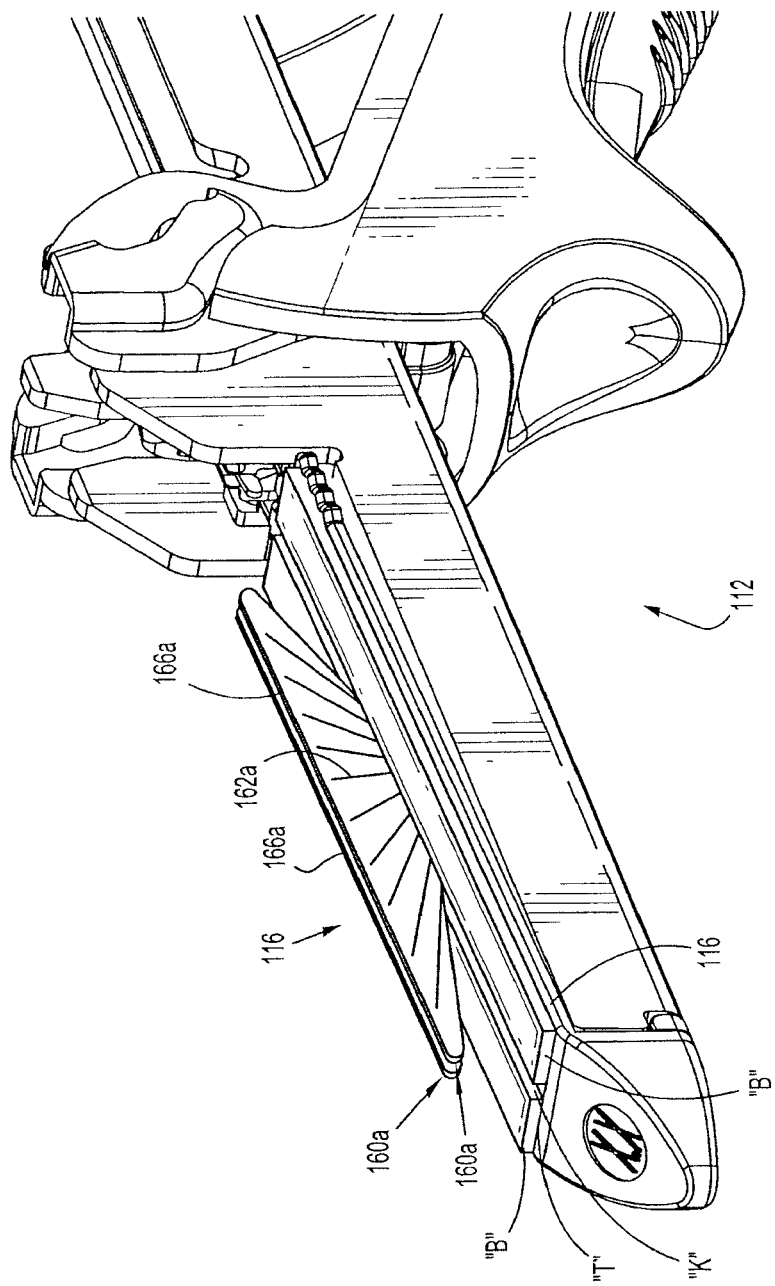
FIG. 5 is an enlarged perspective view of a distal end of the surgical stapling device of FIG. 1, illustrating an alternate buttress attachment feature to the buttress attachment feature of FIG. 4, shown in a first condition.
Figure 5A:
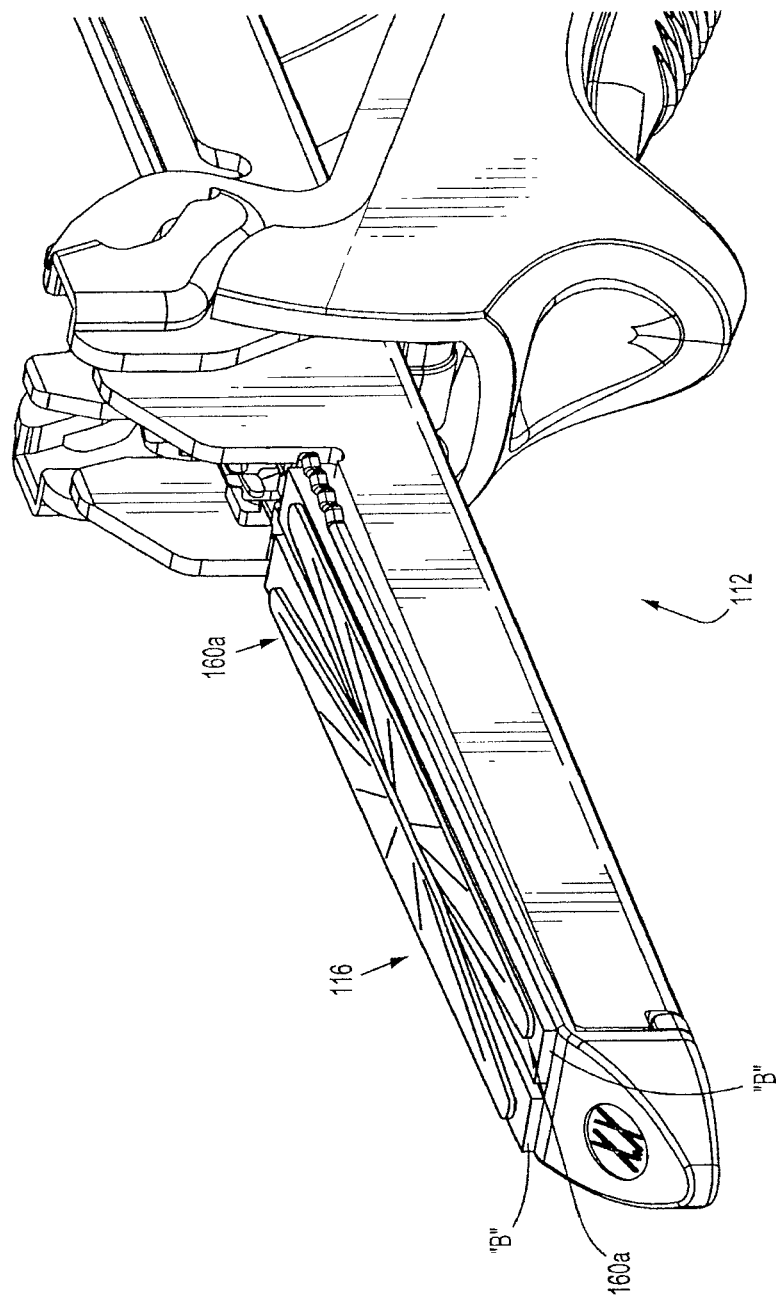
FIG. 5A is an enlarged perspective view of the distal end of the surgical stapling device of FIG. 5, illustrating the buttress attachment feature thereof in a second condition.

Turning now to FIGS. 4 and 4A, a buttress attachment feature, according to another embodiment of the present disclosure, is generally designated as 160a. As shown in FIGS. 4 and 4A, a pair of buttress attachment features 160a extend from opposed sides of distal ends of cartridge receiving half-section 112 and/or anvil half-section 114, however, it is contemplated that in an embodiment, buttress attachment features 160a may extend from knife channel "K" (see FIGS. 5 and 5A).

Each buttress attachment feature 160a includes a plurality of ribs 162a each having a first end positioned on sides of distal ends of cartridge receiving half-section 112 and/or anvil half-section 114 at a location proximate a mid-point thereof, and a second end extending away from sides of distal ends of cartridge receiving half-section 112 and/or anvil half-section 114 and extending along an entire length of the distal ends of cartridge receiving half-section 112 and/or anvil half-section 114, thereby defining a fan-like configuration. Each buttress attachment feature 160a further includes a panel 166a of suitable biocompatible mesh-like material disposed over ribs 162a.

While separate surgical buttresses "B" are shown positioned over staple pockets "P", it is envisioned and contemplated that panels 166a of buttress attachment features 160a may function as the surgical buttresses "B".

As seen in FIG. 4, buttress attachment features 160a have a first position in which ribs 162a and panels 166a are oriented substantially orthogonal relative to tissue contacting surfaces "T" of cartridge assembly 116 and/or anvil plate (not shown). In this orientation, surgical buttresses "B" may be positioned at least partially over staple pockets "P".

As seen in FIG. 4A, buttress attachment features 160a have a second position in which ribs 162a and panels 166a are oriented substantially parallel relative to tissue contacting surfaces "T" of cartridge assembly 116 and/or anvil plate (not shown). In this orientation, ribs 162a and panels 166a function to maintain surgical buttresses "B" in position against tissue contacting surfaces "T" of cartridge assembly 116 and/or anvil plate (not shown).

Alternatively, if panels 166a are to function as surgical buttresses "B", positioning of ribs 162a and panels 166a to the second position results in placement of the surgical buttress into position against tissue contacting surfaces "T" of cartridge assembly 116 and/or anvil plate (not shown).

In the present embodiment, ribs 162a may be fabricated from suitable shape memory materials in a manner similar to fingers 162 disclosed above. In this manner, buttress attachment features 160a may be oriented from the first to the second position, as needed, with a change in the temperature thereof.

Figure 6:
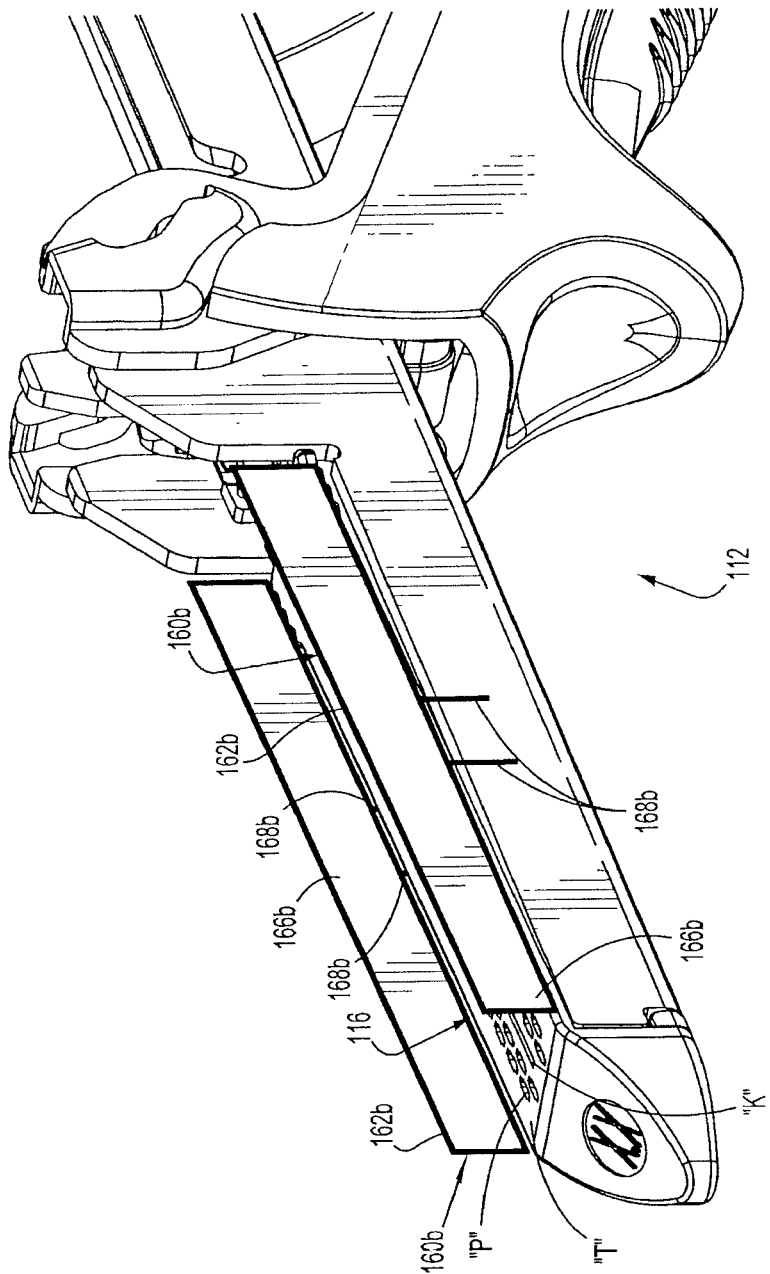
FIG. 6 is an enlarged perspective view of a distal end of the surgical stapling device of FIG. 1, illustrating a buttress attachment feature according to a further embodiment of the present disclosure, shown in a first condition.
Figure 6A:
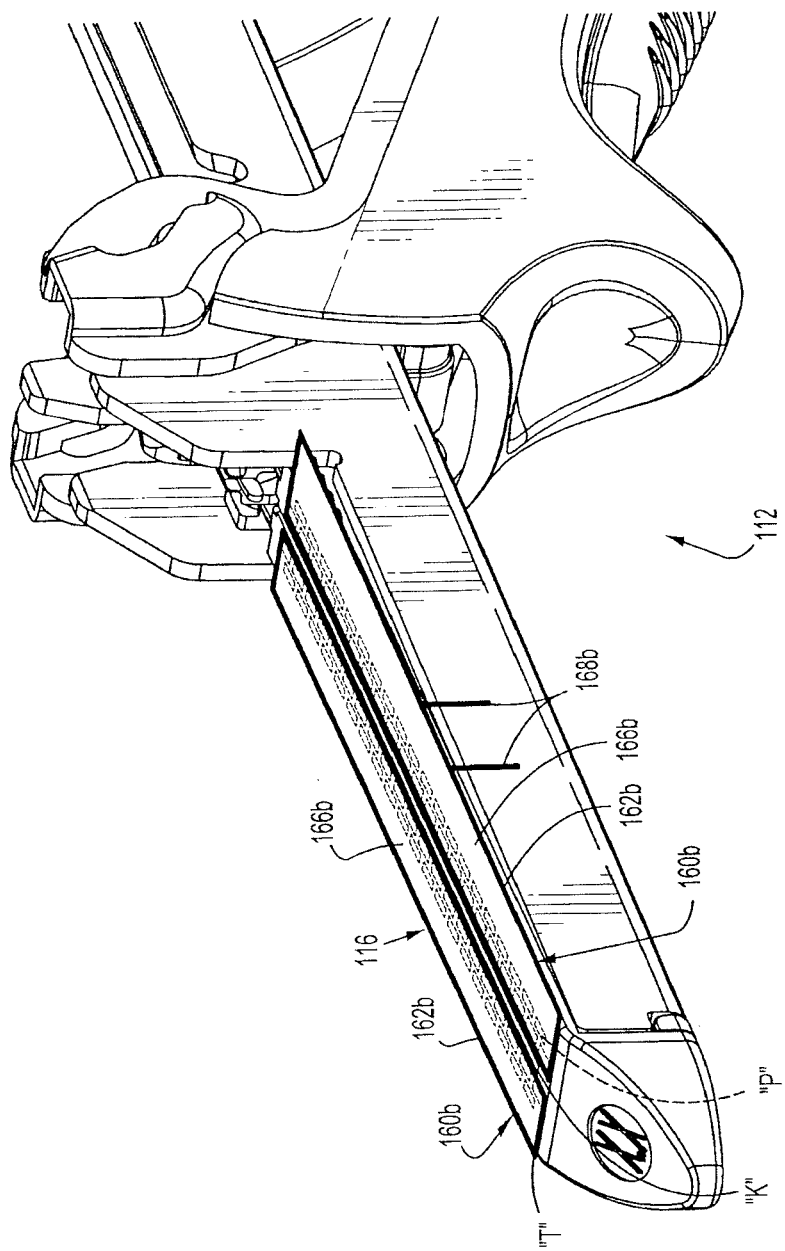
FIG. 6A is an enlarged perspective view of the distal end of the surgical stapling device of FIG. 6, illustrating the buttress attachment feature in a second condition.

Turning now to FIGS. 6 and 6A, a buttress attachment feature, according to another embodiment of the present disclosure, is generally designated as 160b. As shown in FIGS. 6 and 6A, a pair of buttress attachment features 160b extend from opposed sides of distal ends of cartridge receiving half-section 112 and/or anvil half-section 114, however, it is contemplated that in an embodiment, buttress attachment features 160b may extend from knife channel "K" (not shown).

Each buttress attachment feature 160b includes a frame 162b having legs 168b which extend from opposed sides of distal ends of cartridge receiving half-section 112 and/or anvil half-section 114, at a location proximate a mid-point thereof, and a drape 166b supported on and extending over frame 162b. Drape 166b may be fabricated from a suitable biocompatible mesh-like material. In this manner, drape 166b may take the place of surgical buttress "B". However, if desired, a separate surgical buttress "B" may be used in conjunction with buttress attachment feature 160b.

As seen in FIG. 6, buttress attachment features 160b have a first position in which frame 162b and drapes 166b are oriented substantially orthogonal relative to tissue contacting surfaces "T" of cartridge assembly 116 and/or anvil plate (not shown). In this orientation, drapes 166b do not overlie staple pockets "P". Also, in this orientation, separate surgical buttresses (not shown) may, if being used, be positioned at least partially over staple pockets "P".

As seen in FIG. 6A, buttress attachment features 160b have a second position in which frame 162b and drapes 166b are oriented substantially parallel relative to tissue contacting surfaces "T" of cartridge assembly 116 and/or anvil plate (not shown). In this orientation, drapes 166b overlie staple pockets "P" and may act as a surgical buttress. Also, in the present orientation, if a separate surgical buttress (not shown) has been positioned over staple pockets "P" of cartridge assembly 116 and/or anvil plate, frame 162b and drapes 166b function to maintain the separate surgical buttress in position against tissue contacting surfaces "T" of cartridge assembly 116 and/or anvil plate (not shown).

In the present embodiment, frames 162b may be fabricated from suitable shape memory materials in a manner similar to fingers 162 disclosed above. In this manner, buttress attachment features 160b may be oriented from the first to the second position, as needed, with a change in the temperature thereof.

It is contemplated that legs 168b of each buttress attachment feature 160b may extend from knife channel "K", at a location proximate a mid-point thereof.

Figure 7:
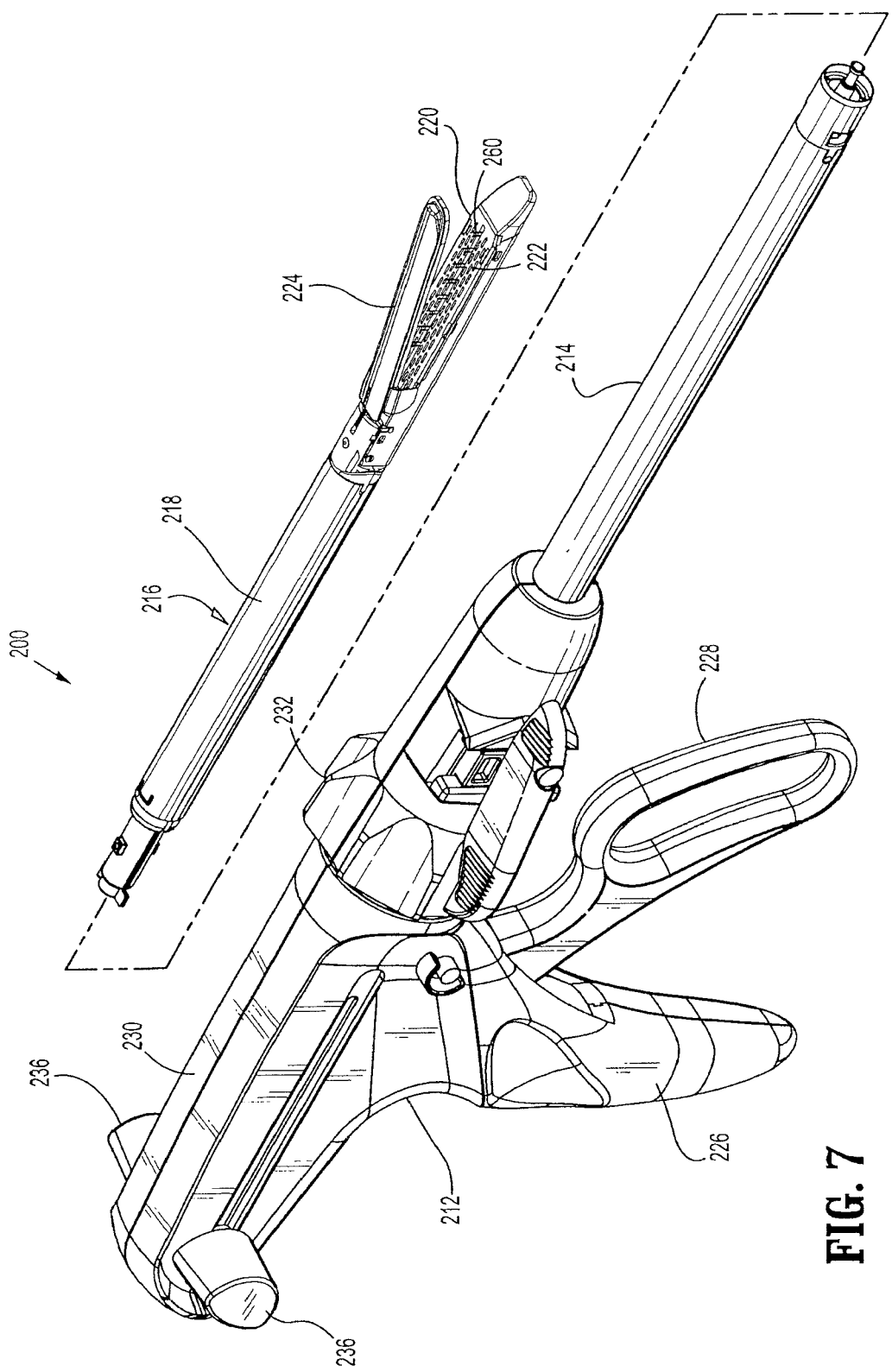
FIG. 7 is a perspective view of an alternative surgical stapling device including a buttress attachment feature, according to any of the embodiments disclosed herein, associated therewith.

Turning now to FIGS. 7-10, a surgical stapling device according to another embodiment of the present disclosure is generally designated as 200. As seen in FIG. 7, surgical stapling device 200 includes a handle assembly 212 and an elongated body 214. The length of elongated body 214 may vary to suit a particular surgical procedure. A disposable loading unit or DLU 216 is releasably secured to a distal end of elongated body 214. DLU 216 includes a proximal body portion 218, which forms an extension of elongated body 214, and a distal tool assembly or end effector 220 including a first member or cartridge assembly 222 and a second member or anvil assembly 224.

Tool assembly 220 is pivotably connected to body 218 about an axis substantially perpendicular to the longitudinal axis of elongated body 214. Cartridge assembly 222 houses a plurality of staples (not shown). Anvil assembly 224 is movable in relation to cartridge assembly 222 between an open position spaced from cartridge assembly 222 and an approximated or clamped position in juxtaposed alignment with cartridge assembly 222.

Handle assembly 212 includes a stationary handle member 226, a movable handle or trigger 228 and a barrel portion 230. A rotatable member 232 is rotatably mounted to the forward end of barrel portion 230 and secured to elongated body 214 to facilitate rotation of elongated body 214 in relation to handle assembly 212. An articulation lever 230a is supported on a distal portion of barrel portion 230 and is operable to effect articulation of tool assembly 220 with respect to body portion 218 of DLU 216. A pair of return knobs 236 are movably supported along barrel portion 230 to effect movement of surgical stapling device 200 from an advanced position to a retracted position.

Reference may be made to U.S. patent application Ser. No. 10/490,790, filed Oct. 4, 2002 (U.S. Patent Publication No. 2004-0232201), the entire content of which is incorporated herein by reference, for a more detailed discussion of the structure and operation of surgical stapling device 200.

As seen in FIGS. 7-10, surgical stapling device 200 includes a buttress attachment feature 260 operatively associated with at least one of the distal end of cartridge assembly 222 and anvil assembly 224. Each buttress attachment feature 260 may include any of the buttress attachment features 160, 160a or 160b described above in regards to surgical stapling device 100 and shown in FIGS. 1-6A. Accordingly, in the interest of clarity and brevity, buttress attachment feature 260 of FIGS. 7-10 is shown and described substantially as buttress attachment feature 160 above.

Figure 8:
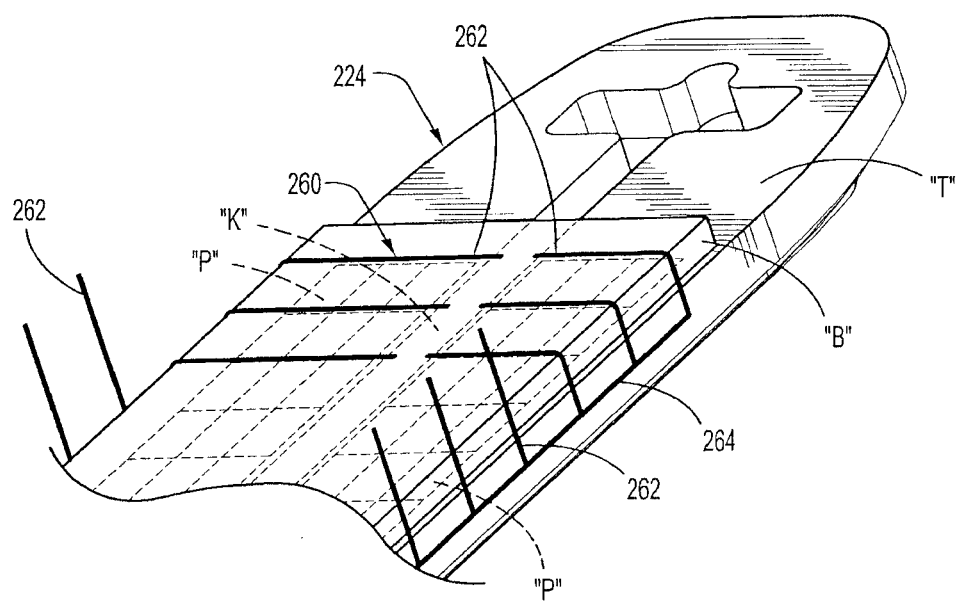
FIG. 8 is an enlarged perspective view of an anvil cartridge of the surgical stapling device of FIG. 7, illustrating the buttress attachment feature thereof in a first and second condition.
Figure 9:
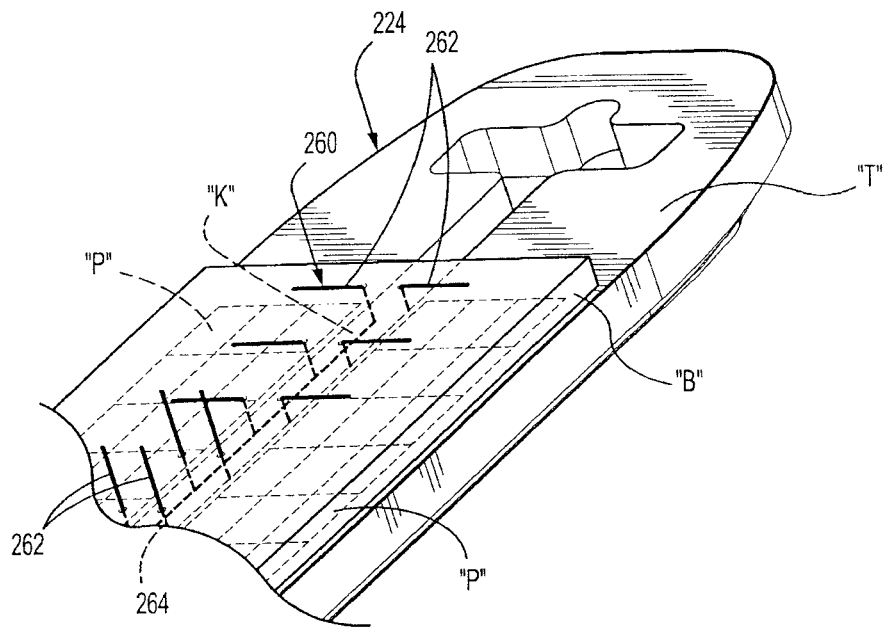
FIG. 9 is an enlarged perspective view of the anvil cartridge of the surgical stapling device of FIG. 7, illustrating an alternate buttress attachment feature thereof in a first and second condition.

As best seen in FIG. 8, each buttress attachment feature 260 includes a plurality of fingers 262 extending from a backspan 264 which backspan 264 is positioned opposed sides of at least one of the distal end of cartridge assembly 222 and anvil assembly 224, however, it is contemplated that in an embodiment, buttress attachment features 260 may extend from knife channel "K" (see FIG. 9).

Fingers 262 have a first position in which fingers 262 extend substantially orthogonal relative to tissue contacting surface "T" of cartridge assembly 222 and/or anvil assembly 224. While in the first position, fingers 262 are oriented so as to enable and/or allow placement and/or removal of surgical buttress "B" into or out of contact with tissue contacting surfaces "T".

Fingers 262 have a second position in which at least a distal or free end of fingers 262 extend substantially parallel to tissue contacting surface "T" of cartridge assembly 222 and/or anvil assembly 224, in a direction towards staple pockets "P" (see FIG. 10) or anvil pockets "P" (see FIG. 9). While in the second position and when a surgical buttress "B" is in position against tissue contacting surface "T" of cartridge assembly 222 and/or anvil assembly 224, fingers 262 are oriented so as to prevent movement and/or removal of surgical buttress "B" relative to and/or from tissue contacting surfaces "T" of cartridge assembly 222 and/or anvil assembly 224.

At least fingers 262 of buttress attachment feature 260 is fabricated from a shape memory alloy (i.e., Nickel Titanium, NiTi, Nitinol, etc.), a shape memory polymer, or any other suitable material exhibiting shape memory properties during elevated temperatures.

Use of buttress attachment feature 260 is substantially similar to use of buttress attachment feature 160 and thus, in the interest of brevity, will not be described in extensive detail hereinbelow.

Figure 10:
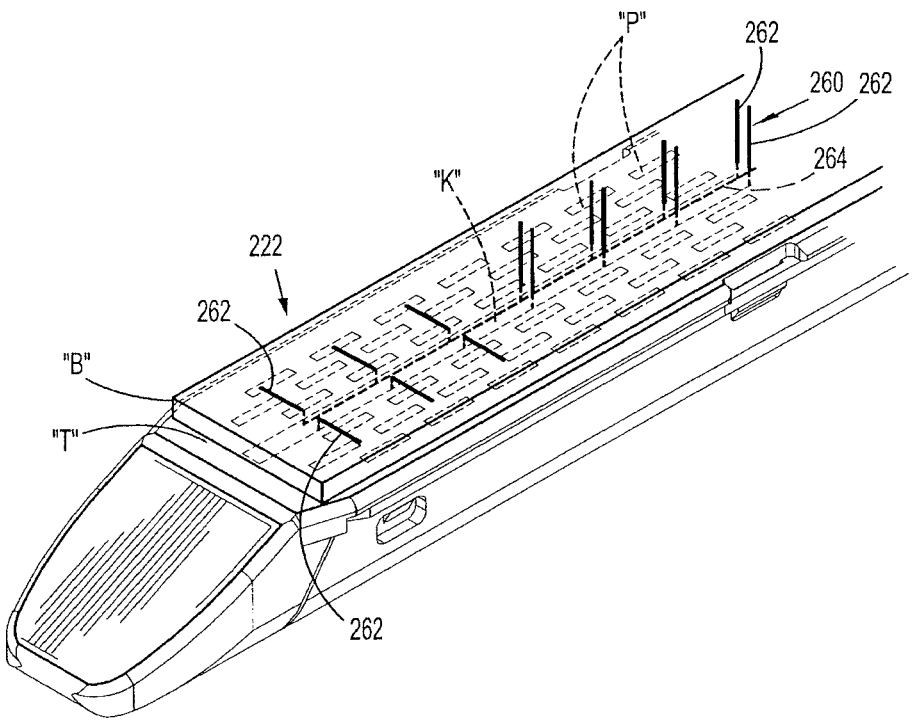
FIG. 10 is an enlarged perspective view of a staple cartridge of the surgical stapling device of FIG. 8, illustrating the buttress attachment feature thereof in a first and second condition, wherein the buttress attachment feature is disposed along a knife channel thereof.

In use, with buttress attachment features 260 at a first temperature, fingers 262 are oriented in the first position, as described above. With fingers 262 in the first position, a surgical buttress "B" may be placed in position against tissue contacting surfaces "T" by placing surgical buttress "B" between fingers 262, as seen in FIG. 8, or by penetrating fingers 262 through surgical buttress "B", as seen in FIGS. 9 and 10. With surgical buttress "B" so positioned, the temperature in the proximity of cartridge assembly 222 and anvil assembly 224 is varied from the first temperature to a second temperature, i.e., either elevated or reduced relative to the first temperature. At the second temperature, buttress attachment features 260 undergo a phase transformation, as described above, wherein free ends of fingers 262 move to the second position, as described above, to secure, maintain, retain or otherwise hold surgical buttress "B" in contact and in position on tissue contacting surface "T" of cartridge assembly 222 and anvil assembly 224.

As seen in FIGS. 8-10, free ends of fingers 262 are shown in a first position near a proximal end of cartridge assembly 222 and anvil assembly 224 and in a second position near a distal end of cartridge assembly 222 and anvil assembly 224. As seen in FIG. 8, when the distal ends of fingers 262 are in the second position, the distal ends of fingers 262 extend toward knife channel "K" and across a width of surgical buttress "B". As seen in FIGS. 9 and 10, when the distal ends of fingers 262 are in the second position, the distal ends of fingers 262 extend away from knife channel "K" and across a width of surgical buttress "B".

With surgical buttress "B" so positioned, the distal end of surgical stapling device 200 may be positioned at the target surgical site with surgical buttress "B" securely held in position against tissue contacting surfaces "T" of cartridge assembly 222 and/or anvil assembly 224. The distal end of surgical stapling device 200 may be introduced to the target surgical site through a trocar, cannula, port or the like.

Buttress attachment features 260 may be positioned on cartridge assembly 222 and/or anvil assembly 224 in such a manner so as to not increase an outer circumferential profile of the distal ends thereof. In this manner, buttress attachment features 260 do not interfere with the placement of the distal end of surgical stapling device 200 at the target surgical site. For example, with buttress attachment features 260 positioned along knife channel "K" (as shown in FIGS. 9 and 10), buttress attachment features 260 do not, at any time, extend beyond an outer profile of distal ends of cartridge assembly 222 and/or anvil assembly 224.

Figure 11:
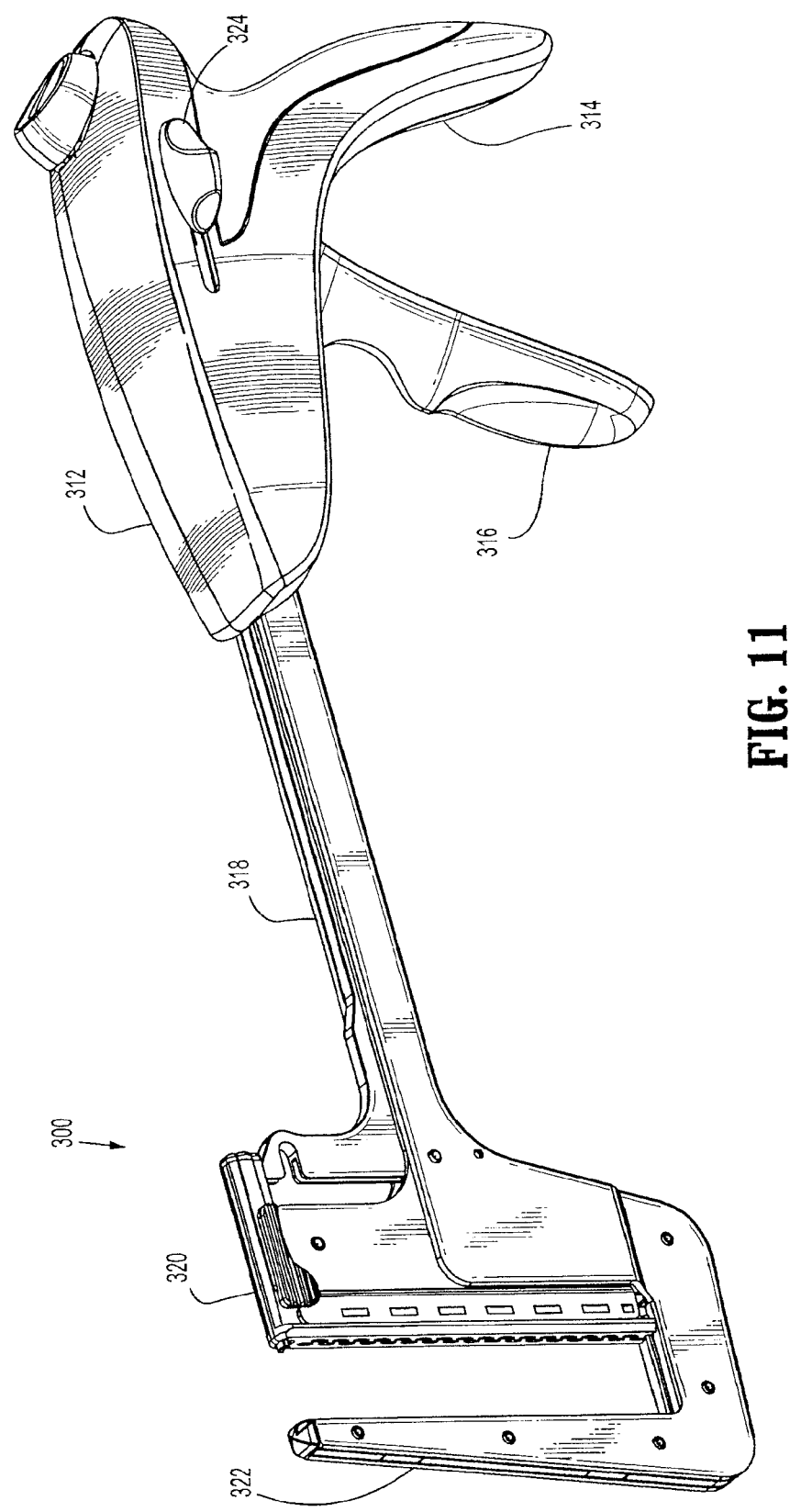
FIG. 11 is a perspective view of yet another alternative surgical stapling device including a buttress attachment feature, according to any of the embodiments disclosed herein, associated therewith.
Figure 12:
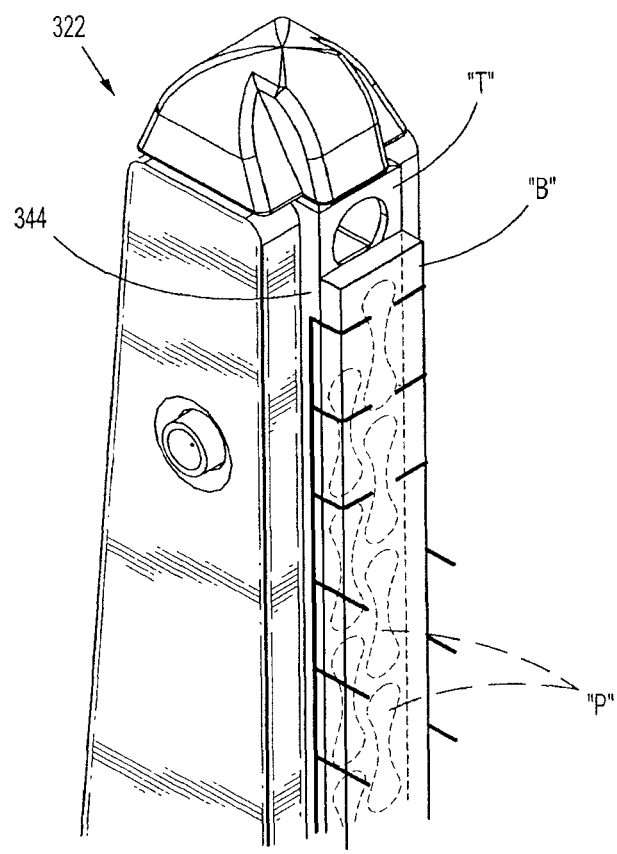
FIG. 12 is an enlarged perspective view of an anvil cartridge of the surgical stapling device of FIG. 11, illustrating the buttress attachment feature thereof in a first and second condition.

Turning now to FIGS. 11 and 12, a surgical stapling device according to another embodiment of the present disclosure is generally designated as 300. As seen in FIG. 11, surgical stapling device 300 includes a body 312 defining a stationary handle 314, a pivotable trigger 316, an elongated central body portion 318, and an end effector including a first member or cartridge assembly 220 and a second member of anvil assembly 322. A thumb button 324 is slidably positioned on each side of body 312. Thumb buttons 324 are movable to manually advance an alignment pin assembly (not shown).

Reference may be made to U.S. patent application Ser. No. 09/687,815, filed Oct. 13, 2000 (Now U.S. Pat. No. 6,817,508), the entire content of which is incorporated herein by reference, for a more detailed discussion of the structure and operation of surgical stapling device 300.

As best seen in FIG. 12, surgical stapling device 300 includes a buttress attachment feature 360 operatively associated with at least one of the cartridge assembly 320 and anvil assembly 322, only buttress attachment feature 360 operatively associated with anvil assembly 322 being shown. Each buttress attachment feature 360 may include any of the buttress attachment features 160, 160a or 160b described above in regards to surgical stapling device 100 and shown in FIGS. 1-6A. Accordingly, in the interest of clarity and brevity, buttress attachment feature 360 of FIGS. 11 and 12 is shown and described substantially as buttress attachment feature 160 above.

As best seen in FIG. 12, each buttress attachment feature 360 includes a plurality of fingers 362 extending from a backspan 364 which backspan 364 is positioned along side of anvil plate 344 of anvil assembly 322.

Fingers 362 have a first position in which fingers 362 extend substantially orthogonal relative to tissue contacting surface "T" of anvil plate 344 of anvil assembly 322. While in the first position, fingers 362 are oriented so as to enable and/or allow placement and/or removal of surgical buttress "B" into or out of contact with tissue contacting surfaces "T".

Fingers 362 have a second position in which at least a distal or free end of fingers 362 extend substantially parallel to tissue contacting surface "T" of anvil plate 344 of anvil assembly 224, in a direction towards anvil pockets "P". While in the second position and when a surgical buttress "B" is in position against tissue contacting surface "T" of anvil plate 344 of anvil assembly 322, fingers 362 are oriented so as to prevent movement and/or removal of surgical buttress "B" relative to and/or from tissue contacting surface "T" of anvil plate 344 of anvil assembly 322.

While buttress attachment feature 360 has been described as associated with anvil assembly 322, a further buttress attachment feature may be provided and associated with cartridge assembly 320, not shown.

At least fingers 362 of buttress attachment feature 360 is fabricated from a shape memory alloy (i.e., Nickel Titanium, NiTi, Nitinol, etc.), a shape memory polymer, or any other suitable material exhibiting shape memory properties during elevated temperatures.

Use of buttress attachment feature 360 is substantially similar to use of buttress attachment feature 160 and thus, in the interest of brevity, will not be described in extensive detail hereinbelow.

In use, with buttress attachment features 360 at a first temperature, fingers 362 are oriented in the first position, as described above. With fingers 362 in the first position, a surgical buttress "B" may be placed in position against tissue contacting surfaces "T" of anvil plate 344 of anvil assembly 322. With surgical buttress "B" so positioned, the temperature in the proximity of anvil assembly 322 is varied from the first temperature to a second temperature, i.e., either elevated or reduced relative to the first temperature. At the second temperature, buttress attachment feature 360 undergoes a phase transformation, as described above, wherein free ends of fingers 362 move to the second position, as described above, to secure, maintain, retain or otherwise hold surgical buttress "B" in contact and in position on tissue contacting surface "T" of anvil plate 344 of anvil assembly 322.

As seen in FIG. 12, free ends of fingers 362 are shown in a first position near a free end of anvil assembly 322 and in a second position near a rear end of anvil assembly 322. When the distal ends of fingers 362 are in the second position, the distal ends of fingers 362 extend toward anvil pockets "P" and across a width of surgical buttress "B".

With surgical buttress "B" so positioned, the distal end of surgical stapling device 300 may be positioned at the target surgical site with surgical buttress "B" securely held in position against tissue contacting surfaces "T" of anvil assembly 322 and/or cartridge assembly 320 (not shown).

Buttress attachment features 360 may be positioned on cartridge assembly 320 and/or anvil assembly 322 in such a manner so as to not increase an outer circumferential profile of the distal ends thereof. In this manner, buttress attachment features 360 do not interfere with the placement of the distal end of surgical stapling device 300 at the target surgical site.

Figure 13:
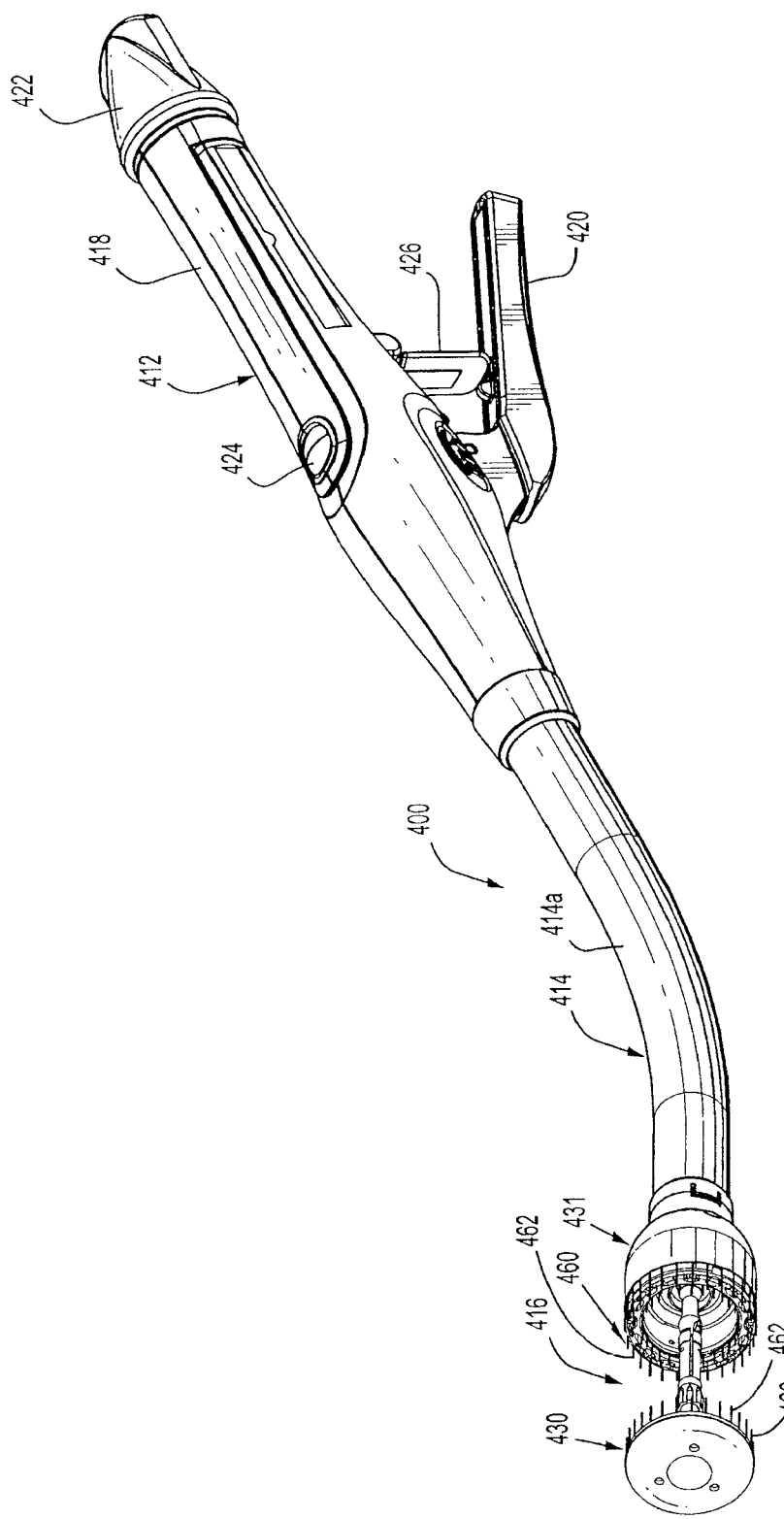
FIG. 13 is a perspective view of still another alternative surgical stapling device including a buttress attachment feature, according to any of the embodiments disclosed herein, associated therewith.
Figure 14:
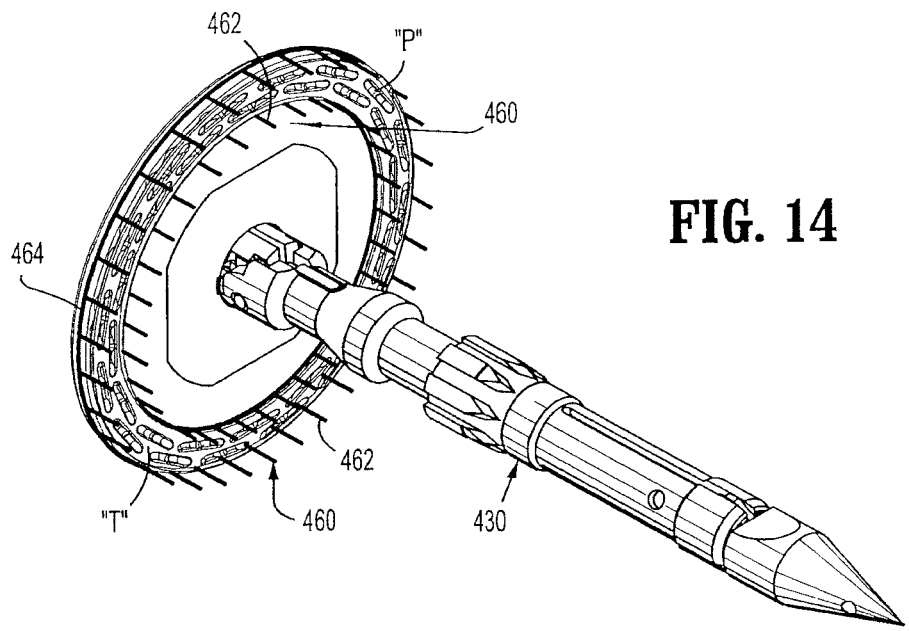
FIG. 14 is an enlarged perspective view of an anvil assembly of the surgical stapling device of FIG. 13, illustrating the buttress attachment feature thereof in a first and second condition.
Figure 15:
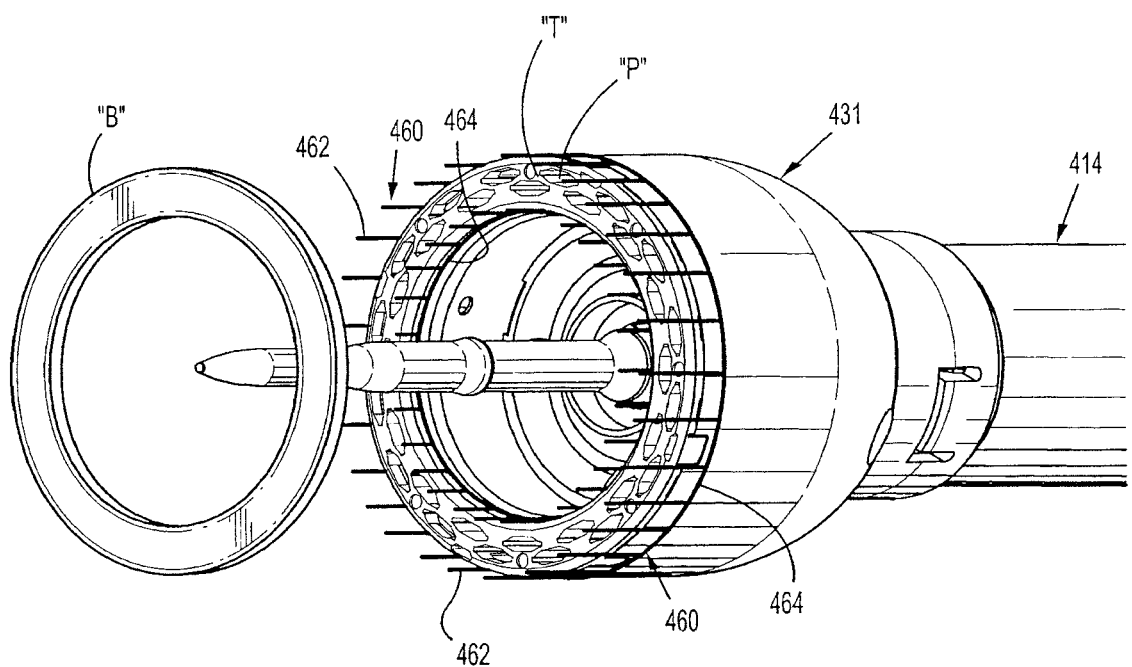
FIG. 15 is an enlarged perspective view of a cartridge assembly of the surgical stapling device of FIG. 13, illustrating the buttress attachment feature thereof in a first and second condition.

Turning now to FIGS. 13-15, a surgical stapling device according to another embodiment of the present disclosure is generally designated as 400. As seen in FIG. 13, surgical stapling device 400 includes a proximal handle assembly 412, an elongated central body portion 414 including a curved elongated outer tube 414a, and a distal head portion 416. Alternately, in some surgical procedures, e.g., the treatment of hemorrhoids, it is desirable to have a substantially straight, preferably shortened, central body portion. The length, shape and/or the diameter of body portion 414 and head portion 416 may also be varied to suit a particular surgical procedure.

Handle assembly 412 includes a stationary handle 418, a firing trigger 420, a rotatable approximation knob 422 and an indicator 424. Stationary handle 418 defines a housing for the internal components of handle assembly 412. The internal components of handle portion 412 will be discussed in detail below. A pivotally mounted trigger lock 426 is fastened to handle assembly 412 and is manually positioned to prevent inadvertent firing of surgical stapling device 400. Indicator 424 is positioned on the stationary handle 418 and includes indicia, e.g., color coding, alpha-numeric labeling, etc., to identify to a surgeon whether the device is approximated and is ready to be fired. Head portion 416 includes an anvil assembly 430 and a cartridge assembly 431. Each of these assemblies will be discussed in detail below.

Reference may be made to U.S. patent application Ser. No. 10/528,975, filed Oct. 6, 2003 (now U.S. Pat. No. 7,303,106), the entire content of which is incorporated herein by reference, for a more detailed discussion of the structure and operation of surgical stapling device 400.

As seen in FIGS. 13-15, surgical stapling device 400 includes a buttress attachment feature 460 operatively associated with at least one of cartridge assembly 431 and anvil assembly 430. Each buttress attachment feature 460 may include any of the buttress attachment features 160, 160a or 160b described above in regards to surgical stapling device 100 and shown in FIGS. 1-7. Accordingly, in the interest of clarity and brevity, buttress attachment feature 460 of FIGS. 13-15 is shown and described substantially as buttress attachment feature 160 above.

As best seen in FIGS. 14 and 15, each buttress attachment feature 460 includes a plurality of fingers 462 extending from a backspan 464 which backspan 464 is positioned alongside at least one of staple pockets "P" of cartridge assembly 431 and alongside anvil pockets "P" of anvil assembly 430. While buttress attachment features 460 are shown positioned around the periphery or circumference of cartridge assembly 431 and/or anvil assembly 430 and along both sides of staple pockets "P" of cartridge assembly 431 and/or anvil pockets "P" of anvil assembly 430, it is envisioned and within the scope of the present disclosure for buttress attachment features 460 to be placed along only one side of staple pockets "P" of cartridge assembly 431 and/or anvil pockets "P" of anvil assembly 430 (not shown). It is further envisioned and within the scope of the present disclosure for buttress attachment features 460 to extend only along a portion of the periphery of or circumference of cartridge assembly 431 and/or anvil assembly 430.

Fingers 462 have a first position in which fingers 462 extend substantially orthogonal relative to tissue contacting surface "T" of cartridge assembly 431 and/or anvil assembly 430. While in the first position, fingers 462 are oriented so as to enable and/or allow placement and/or removal of surgical buttress "B" into or out of contact with tissue contacting surfaces "T".

Fingers 462 have a second position in which at least a distal or free end of fingers 462 extend substantially parallel to tissue contacting surface "T" of cartridge assembly 431 and/or anvil assembly 430, in a direction towards anvil pockets "P" (see FIG. 14) or staple pockets "P" (see FIG. 15). While in the second position and when a surgical buttress "B" is in position against tissue contacting surface "T" of cartridge assembly 431 and/or anvil assembly 430, fingers 462 are oriented so as to prevent movement and/or removal of surgical buttress "B" relative to and/or from tissue contacting surfaces "T" of cartridge assembly 431 and/or anvil assembly 430.

At least fingers 462 of buttress attachment feature 460 is fabricated from a shape memory alloy (i.e., Nickel Titanium, NiTi, Nitinol, etc.), a shape memory polymer, or any other suitable material exhibiting shape memory properties during elevated temperatures.

Use of buttress attachment feature 460 is substantially similar to use of buttress attachment feature 160 and thus, in the interest of brevity, will not be described in extensive detail hereinbelow.

In use, with buttress attachment features 460 at a first temperature, fingers 462 are oriented in the first position, as described above. With fingers 462 in the first position, a surgical buttress "B" may be placed in position against tissue contacting surfaces "T" by penetrating fingers 462 through surgical buttress "B". With surgical buttress "B" so positioned, the temperature in the proximity of cartridge assembly 431 and anvil assembly 430 is varied from the first temperature to a second temperature, i.e., either elevated or reduced relative to the first temperature. At the second temperature, buttress attachment features 460 undergo a phase transformation, as described above, wherein free ends of fingers 462 move to the second position, as described above, to secure, maintain, retain or otherwise hold surgical buttress "B" in contact and in position on tissue contacting surface "T" of cartridge assembly 431 and anvil assembly 430.

With surgical buttress "B" so positioned, the distal end of surgical stapling device 400 may be positioned at the target surgical site with surgical buttress "B" securely held in position against tissue contacting surfaces "T" of cartridge assembly 431 and/or anvil assembly 430. The distal end of surgical stapling device 400 may be introduced to the target surgical site through a trocar, cannula, port or the like.

Buttress attachment features 460 may be positioned on cartridge assembly 431 and/or anvil assembly 430 in such a manner so as to not increase an outer circumferential profile of the distal ends thereof, i.e., along an inner circumference thereof and adjacent staple or anvil pockets "P". In this manner, buttress attachment features 460 do not interfere with the placement of the distal end of surgical stapling device 400 at the target surgical site.

Surgical buttresses "B" may be made of biocompatible, non-absorbable material commercially known as "TEFLON" which is a registered trademark owned by DuPont de Nemours & Co., or cotton, which is non-absorbable and can be implanted in the body without adverse effects, or other substances which are absorbable by the body such as "VICRYL" which is a registered trademark of Johnson & Johnson or "DEXON" which is a registered trademark of Davis and Geck. Additionally, it is envisioned that surgical buttress "B" may be manufactured from natural-animal derived material (e.g., collagen, pericardium, etc.) or synthetic materials (e.g., poly(lactic acid), poly(glycolic acid), poly(caprolactone), poly(trimethylene carbonate), polydioxanone, p(orthoesters), poly(alkylene oxides)). One exemplary surgical buttress "B" which may be used is "SEAMGUARD" which is a registered trademark owned by W. L. Gore & Associates, Inc, or "PERI-STRIPS" which is a registered trademark owned by Synovis Surgical Innovations, a division of Synovis Life Technologies, Inc. Surgical buttress "B" may include any combination of materials disclosed herein or incorporated herein by reference.

Surgical buttresses "B" may include any of the surgical buttresses disclosed and described in U.S. application Ser. No. 11/248,846, filed on Oct. 12, 2005 (now U.S. Pat. No. 7,823,592), the entire content of which is incorporated herein by reference.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A cartridge assembly configured for selective, removable connection to a cartridge receiving section of a surgical stapling device, the cartridge assembly comprising:
a tissue contacting surface defining:
a plurality of staple retaining pockets formed therein, wherein the plurality of staple retaining pockets are arranged in parallel, longitudinally extending rows; and
a longitudinally extending knife slot; and
at least one buttress attachment feature for selectively securing a surgical buttress adjacent the tissue contacting surface, the buttress attachment feature movable between a first position in which a free end of the buttress attachment feature permits placement of a surgical buttress against the tissue contacting surface, and a second position in which the free end of the buttress attachment feature retains the surgical buttress against the tissue contacting surface, wherein the buttress attachment feature is responsive to a temperature change such that the buttress attachment feature is in the first portion when the buttress attachment features is at a first temperature and in the second position when the buttress attachment feature is at a second temperature, the second temperature being greater than the first temperature, wherein the buttress attachment feature comprises a shape memory alloy that is responsive to the temperature change.

2. The cartridge assembly according to claim 1, wherein in the first position, the free end of the buttress attachment feature extends substantially orthogonally with respect to the tissue contacting surface, and in the second position the free end of the buttress attachment extends substantially parallel with respect to the tissue contacting surface.

3. The cartridge assembly according to claim 1, wherein the buttress attachment features includes a backspan configured to secure the surgical buttress.

4. The cartridge assembly according to claim 1, wherein the buttress attachment feature includes a frame configured to secure the surgical buttress.

5. The cartridge assembly according to claim 4, wherein the frame supports a drape positioned to overlie the portion of the tissue contacting surface when the buttress attachment feature is in the second position.

6. The cartridge assembly according to claim 5, wherein the drape comprises the surgical buttress.

7. The cartridge assembly according to claim 1, wherein the buttress attachment feature includes a plurality of fingers spaced along the longitudinally extending knife slot of the cartridge assembly.

8. The cartridge assembly according to claim 7, wherein the plurality of fingers extends along opposed sides of the longitudinally extending knife slot of the cartridge assembly.

9. The cartridge assembly according to claim 7, wherein each of the plurality of fingers is oriented to extend substantially orthogonal to the first tissue contacting surface when the buttress attachment feature is in the first position, and substantially parallel to the first tissue contacting surface when the buttress attachment feature is in the second position.

10. The cartridge assembly according to claim 7, wherein the plurality of fingers comprises a shape memory alloy.

11. The cartridge assembly according to claim 10, wherein the shape memory alloy is a nickel titanium alloy.

12. The cartridge assembly according to claim 7, wherein each of the plurality of fingers is configured to penetrate the surgical buttress when the buttress attachment feature is in the first position, and to overlie the first tissue contacting surface when the buttress attachment feature is in the second position.

13. A cartridge assembly configured for selective, removable connection to a cartridge receiving section of a surgical stapling device, the cartridge assembly comprising:

a tissue contacting surface defining:
  a plurality of staple retaining pockets formed therein, where in the plurality of staple retaining pockets are arranged in parallel, longitudinally extending rows; and
  a longitudinally extending knife slot; and
at least one buttress attachment feature for selectively securing a surgical buttress adjacent the tissue contacting surface, the buttress attachment feature including a shape memory alloy, wherein the shape memory alloy is configured to assume a first orientation with respect to the tissue contacting surface at a first temperature wherein a free end of the buttress attachment feature is spaced from the tissue contacting surface for permitting movement of the surgical buttress with respect to the tissue contacting surface, and wherein the shape memory alloy is configured to assume a second orientation with respect to the tissue contacting surface at a second temperature where the free end of the buttress attachment feature is relatively proximate to the tissue contacting surface for securing the surgical buttress to the tissue contacting surface.

14. The cartridge assembly according to claim 13, wherein the second temperature is greater than the first temperature.

15. The cartridge assembly according to claim 13, wherein the buttress attachment feature includes a plurality of fingers spaced along the knife slot.

16. The cartridge assembly 15, wherein each of the plurality of fingers is oriented to extend substantially orthogonal to the first tissue contacting surface when the buttress attachment feature is in the first position, and substantially parallel to the first tissue contacting surface when the buttress attachment feature is in the second position.

17. A method of performing a surgical procedure, comprising the steps of:
  providing a surgical stapling device including:
    a cartridge assembly receiving section of a jaw assembly; and
    an anvil assembly, wherein a tissue contacting surface is defined by at least one of the cartridge assembly and the supporting section of the jaw assembly;
  providing a cartridge assembly configured for selective, removable connection to the cartridge receiving section of the surgical stapling device, the cartridge assembly including:
    a tissue contacting surface defining:
      a plurality of staple retaining pockets formed therein, wherein the plurality of staple retaining pockets are arranged in parallel, longitudinally extending rows; and
      a longitudinally extending knife slot; and
    at least one buttress attachment feature for selectively securing a surgical buttress adjacent the tissue contacting surface, the buttress attachment feature including a shape memory allow, wherein the shape memory alloy is configured to assume a first orientation with respect to the tissue contacting surface wherein a free end of the buttress attachment feature is spaced from the tissue contacting surface, and wherein the shape memory alloy is configured to assume a second orientation with respect to the tissue contacting surface wherein the free end of the buttress attachment feature is relatively proximate to the tissue contacting surface;
  providing a surgical buttress;
  placing the surgical buttress against the tissue contacting surface of the cartridge assembly when the buttress attachment feature in the first position and loading the cartridge assembly into the cartridge receiving section of the surgical stapling device; and
  heating the buttress attachment feature to move the buttress attachment feature from the first position to the second position.

18. The method according to claim 17, wherein the surgical buttress is placed against the tissue contacting surface of the cartridge assembly prior to the step of loading the cartridge assembly into the cartridge receiving half-section of the surgical stapling device.

\* \* \* \* \*